US005522790A

United States Patent [19]
Moll et al.

[11] Patent Number: 5,522,790
[45] Date of Patent: Jun. 4, 1996

[54] RETRACTION APPARATUS AND METHODS FOR ENDOSCOPIC SURGERY

[75] Inventors: Frederic H. Moll, San Francisco; Albert K. Chin, Palo Alto, both of Calif.

[73] Assignee: Origin Medsystems, Inc., Menlo Park, Calif.

[21] Appl. No.: 212,122

[22] Filed: Mar. 14, 1994

Related U.S. Application Data

[60] Division of Ser. No. 877,955, May 4, 1992, Pat. No. 5,361,752, which is a continuation-in-part of Ser. No. 794,590, Nov. 19, 1991, Pat. No. 5,309,896, which is a continuation-in-part of Ser. No. 706,781, May 29, 1991, abandoned.

[51] Int. Cl.⁶ .................................................... A61B 17/02
[52] U.S. Cl. ...................... 600/204; 600/206; 600/207; 600/208; 600/211; 606/198
[58] Field of Search .................................. 606/198, 195, 606/192; 604/105; 600/204, 206, 207, 209, 211, 208

[56] References Cited

U.S. PATENT DOCUMENTS

| 1,060,350 | 4/1913 | Miller . |
| 1,275,520 | 8/1918 | Bell . |

(List continued on next page.)

FOREIGN PATENT DOCUMENTS

| 516114 | 5/1981 | Australia | A61B 10/00 |
| 0010650 | 5/1980 | European Pat. Off. | A61M 31/00 |
| 0246086 | 11/1987 | European Pat. Off. | A61B 17/02 |
| 0251976 | 1/1988 | European Pat. Off. | A61M 29/02 |
| 0275230 | 7/1988 | European Pat. Off. | A61M 25/00 |
| 0411767A | 2/1991 | European Pat. Off. | A61B 19/00 |
| WO91/01687 | 2/1991 | European Pat. Off. | A16B 8/12 |
| 2474304 | 7/1981 | France | A61B 17/00 |
| 2646088 | 10/1990 | France | A61M 29/04 |
| 2847633 | 5/1979 | Germany | A61B 17/22 |
| 9104383 | 7/1991 | Germany | A61B 17/02 |
| 797668 | 6/1978 | U.S.S.R. | A16B 17/02 |
| 13679478 | 3/1985 | U.S.S.R. | A61B 17/02 |
| 502331 | 9/1937 | United Kingdom . |
| 2071502 | 9/1981 | United Kingdom | A61B 17/02 |

OTHER PUBLICATIONS

A. G. Gordon, et al., "The Development of Laparoscopy Surgery," Baillère's Clinical Obstetrics and Gynaecology, vol. 3, No. 3, Sep. 1989, pp. 429–449.

(List continued on next page.)

*Primary Examiner*—Michael H. Thaler
*Attorney, Agent, or Firm*—Limbach & Limbach

[57] ABSTRACT

A first inflatable retraction device has a first inflatable chamber and a non-pressurized chamber inside the main chamber. The non-pressurized chamber is expanded by inflating a second inflatable chamber. The non-pressurized chamber enables the main chamber to remain inflated when an aperture is cut in the envelope of the main chamber, through which treatment is carried out. A second inflatable retraction device has an inflatable retractor and a maintainer. The inflatable retractor retracts the organ and the maintainer maintains the organ in its retracted condition after the inflatable retractor is deflated. The maintainer can be inflatable, and can be inside or outside the inflatable retractor. A self-retracting endoscope has an optical assembly with an expandable retractor fitted to its distal end. The distal end of the endoscope is inserted into the body with the retractor in a collapsed condition. The retractor is then expanded to retract organs that would otherwise obstruct the view from the distal end of the optical assembly. After observations are complete, the retractor is returned to its collapsed condition. An insertion tube enables cylindrical objects, such as packaged inflatable retraction devices, to be pulled, instead of pushed, into the body. The additional chamber of an inflatable retraction device having two inflatable chambers is filled with a slurry of a particulate solid in a liquid. The liquid is removed and the additional chamber evacuated to consolidate the particulate solid. This increases the retracting strength of the additional chamber.

12 Claims, 14 Drawing Sheets

U.S. PATENT DOCUMENTS

| | | | |
|---|---|---|---|
| 1,735,519 | 11/1929 | Vance . | |
| 1,947,649 | 2/1934 | Kadavy | 128/20 |
| 2,663,020 | 12/1953 | Cushman | 2/2 |
| 2,854,983 | 10/1958 | Baskin | 604/105 X |
| 3,039,468 | 6/1962 | Price | 128/347 |
| 3,173,418 | 3/1965 | Baran | 128/351 |
| 3,626,949 | 12/1971 | Shute | 128/344 |
| 3,774,596 | 11/1973 | Cook | 128/5 |
| 3,782,370 | 1/1974 | McDonald | 128/20 |
| 3,800,788 | 4/1974 | White | 128/83 |
| 3,817,251 | 6/1974 | Hasson | 128/348 |
| 3,831,587 | 8/1974 | Boyd et al. | 128/4 |
| 3,863,639 | 2/1975 | Kleaveland | 128/303 R |
| 3,882,852 | 5/1975 | Sinnreich | 128/4 |
| 3,961,632 | 7/1976 | Moossun | 128/347 |
| 4,077,412 | 3/1978 | Moossun | 128/347 |
| 4,083,369 | 4/1978 | Sinnreich | 128/276 |
| 4,137,906 | 2/1979 | Akiyama et al. | 128/2 A |
| 4,157,085 | 6/1979 | Austad | 128/1 |
| 4,183,102 | 1/1980 | Guiset | 604/101 |
| 4,198,981 | 4/1980 | Sinnreich | 128/344 |
| 4,217,889 | 8/1980 | Radovan et al. | 128/1 |
| 4,240,433 | 12/1980 | Bordow | 128/347 |
| 4,254,762 | 3/1981 | Yoon | 128/4 |
| 4,263,900 | 4/1981 | Nicholson | 128/20 |
| 4,271,839 | 6/1981 | Fogarty et al. | 128/344 |
| 4,291,687 | 9/1981 | Sinnreich | 128/129 |
| 4,318,410 | 3/1982 | Chin | 128/325 |
| 4,357,940 | 11/1982 | Muller | 128/303 R |
| 4,430,076 | 2/1984 | Harris | 604/96 |
| 4,447,227 | 5/1984 | Kotsanis | 604/95 |
| 4,493,711 | 1/1985 | Chin et al. | 604/271 |
| 4,517,979 | 5/1985 | Pacenka | 606/195 |
| 4,535,773 | 8/1985 | Yoon | 604/51 |
| 4,574,780 | 3/1986 | Manders | 128/1 |
| 4,598,699 | 7/1986 | Garren et al. | 128/4 |
| 4,601,710 | 7/1986 | Moll | 604/165 |
| 4,612,938 | 9/1986 | Dietrich et al. | 128/655 |
| 4,615,704 | 10/1986 | Frisch | 623/8 |
| 4,648,383 | 3/1987 | Angelchik | 606/198 X |
| 4,651,717 | 3/1987 | Jakubczak | 128/344 |
| 4,654,030 | 3/1987 | Moll et al. | 604/165 |
| 4,666,447 | 5/1987 | Smith et al. | 623/8 |
| 4,709,697 | 12/1987 | Muller | 128/303 R |
| 4,719,918 | 1/1988 | Bonomo et al. | 128/344 |
| 4,723,549 | 2/1988 | Wholey et al. | 604/101 X |
| 4,739,762 | 4/1988 | Palmaz | 128/343 |
| 4,763,653 | 8/1988 | Rockey | 128/344 |
| 4,775,371 | 10/1988 | Mueller, Jr. | 604/280 |
| 4,779,611 | 10/1988 | Grooters et al. | 128/4 |
| 4,800,901 | 1/1989 | Rosenberg | 128/899 |
| 4,803,029 | 2/1989 | Iversen et al. | 264/264 |
| 4,863,440 | 9/1989 | Chin | 604/271 |
| 4,878,495 | 11/1989 | Grayzel | 128/344 |
| 4,919,152 | 4/1990 | Ger | 128/898 |
| 4,944,443 | 7/1990 | Oddsen et al. | 227/19 |
| 4,966,583 | 10/1990 | Debbas | 604/98 |
| 4,976,710 | 12/1990 | Mackin | 606/15 |
| 4,984,564 | 1/1991 | Yuen | 128/20 |
| 5,002,557 | 3/1991 | Hasson | 606/191 |
| 5,007,898 | 4/1991 | Rosenbluth et al. | 604/54 |
| 5,049,132 | 9/1991 | Shaffer et al. | 604/101 |
| 5,083,576 | 1/1992 | Ruiz-Razura et al. | 128/898 |
| 5,103,804 | 4/1992 | Abele et al. | 128/4 |
| 5,109,875 | 5/1992 | Gottlieb | 128/899 |
| 5,116,357 | 5/1992 | Eberbach | 606/213 |
| 5,122,122 | 6/1992 | Allgood | 604/174 |
| 5,158,548 | 10/1992 | Lau et al. | 604/96 |
| 5,163,949 | 11/1992 | Bonutti | 606/192 |
| 5,176,697 | 1/1993 | Hasson et al. | 606/191 |
| 5,178,133 | 1/1993 | Pena | 128/20 |
| 5,183,464 | 2/1993 | Dubrul et al. | 128/3 |
| 5,183,468 | 2/1993 | McLees | 604/164 |
| 5,188,596 | 2/1993 | Condon et al. | 604/101 |
| 5,188,630 | 2/1993 | Christoudias | 606/1 |
| 5,195,507 | 3/1993 | Bilweis | 128/20 |
| 5,197,948 | 3/1993 | Ghodsian | 604/30 |
| 5,197,971 | 3/1993 | Bonutti | 606/192 |
| 5,275,610 | 1/1994 | Eberbach | 604/105 X |
| 5,331,975 | 7/1994 | Bonutti | 128/898 |

OTHER PUBLICATIONS

R. Wittmoser, "Retroperitoneoscopy: A Preliminary Report", *Endoscopy*, 1976, pp. 760–761.

Charles G. Neumann, M. D., "The Expansion of the Area of the Skin by Progressive Disention of a Subcutaneous Balloon", Plastic and Reconstructive Surgery, Feb. 1957, vol. 19, No. 2, pp. 124–130.

*ed. G. Berci, Endoscopy, Appleton–Century–Crofts,1976, pp. 382–85 and 412.

*Unknown—Laparoscopy for Sterlization, Section 1, A Chronology of Laparoscopy.

*"New Surgical Procedures for Indirect Hernias"—Product leaflet for Herniastat™ disposable automatic surgical stapling device published by Innovative Surgical Devices, Inc., date unknown.

*"A Tiny TV Camera is Fast Transforming Gallbladder Surgery," Wall Street Journal, Dec. 10, 1990, p. A1, continued on p. A5.

*A Comprehensive Guide to Purchasing [Hospital Supplies], V. Mueller & Co., Chicago, 1956, p. 829.

*H. Nagai et al., A New Method of Laparoscopic Cholecystectomy: An Abdominal Wall Lifting Technique Without Pneumoperitoneum, Surgical Laparoscopy and Endoscopy, vol. 1, No. 2, 1991, p. 126.

*M. M. Gazayerli, "The Gazayerli Endoscopic Retractor Model 1," Surgical Laparoscopy and Endoscopy, vol. 1, No. 2, 1991, pp. 98–100.

*Geza J. Jako & Stephen Rozsos, "Preliminary Report: Endoscopic Laser Microsurgical Removal of Human Gallbladder," J. Laparoendoscopic Surgery, vol. 1, No. 4, 1991.

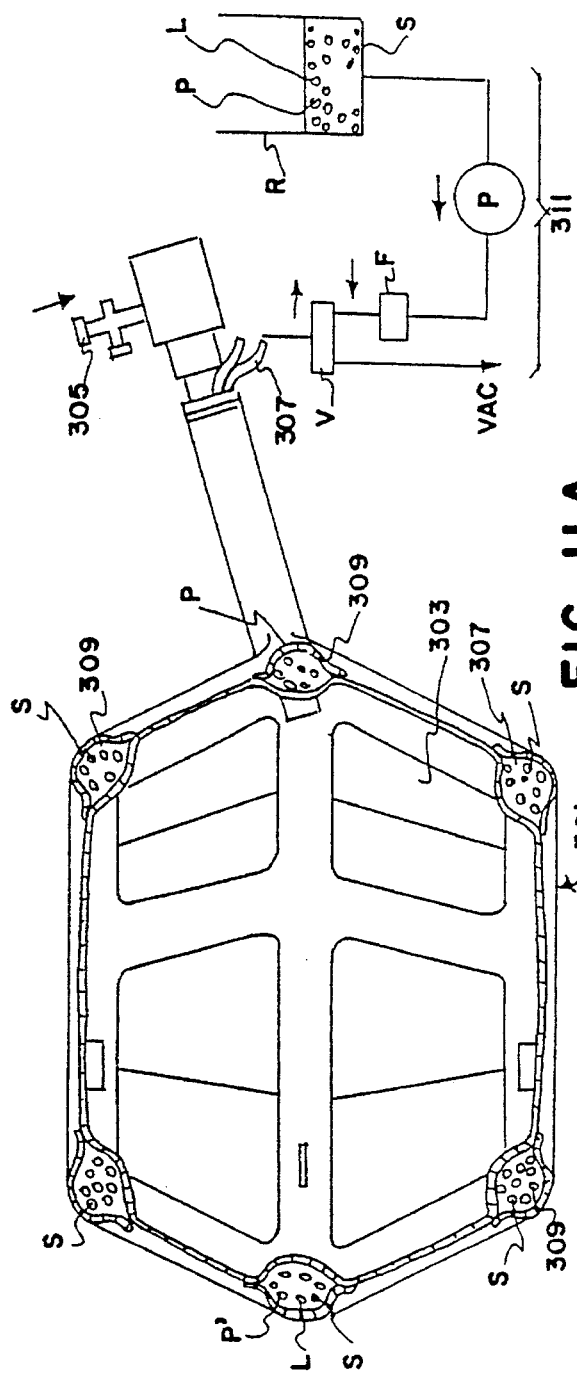
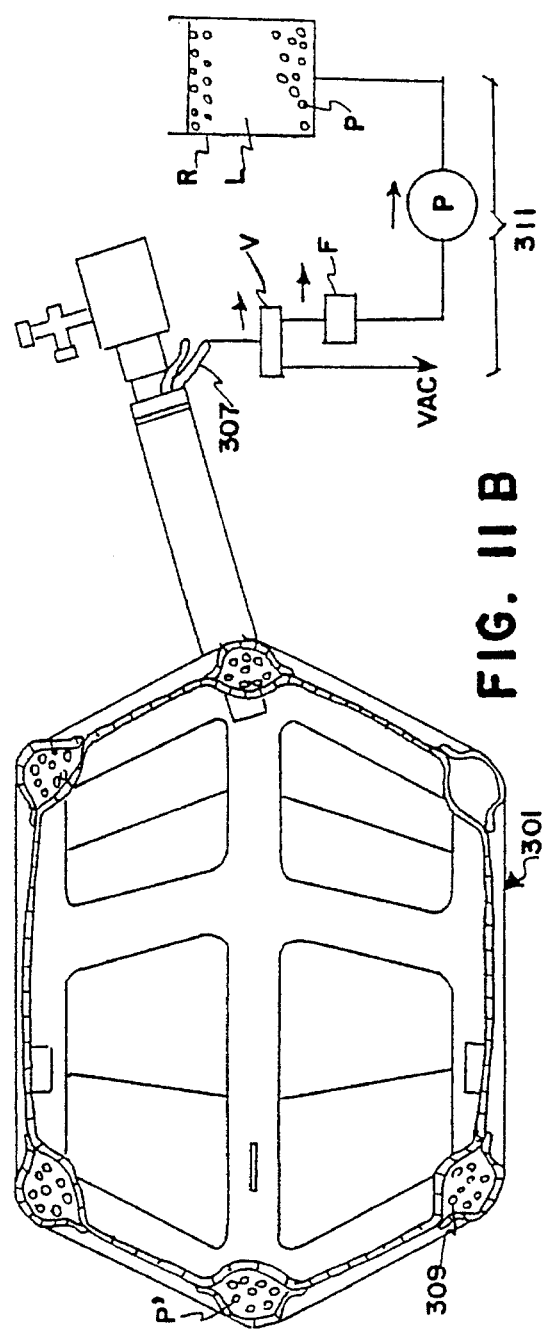
FIG. 11A
FIG. 11B

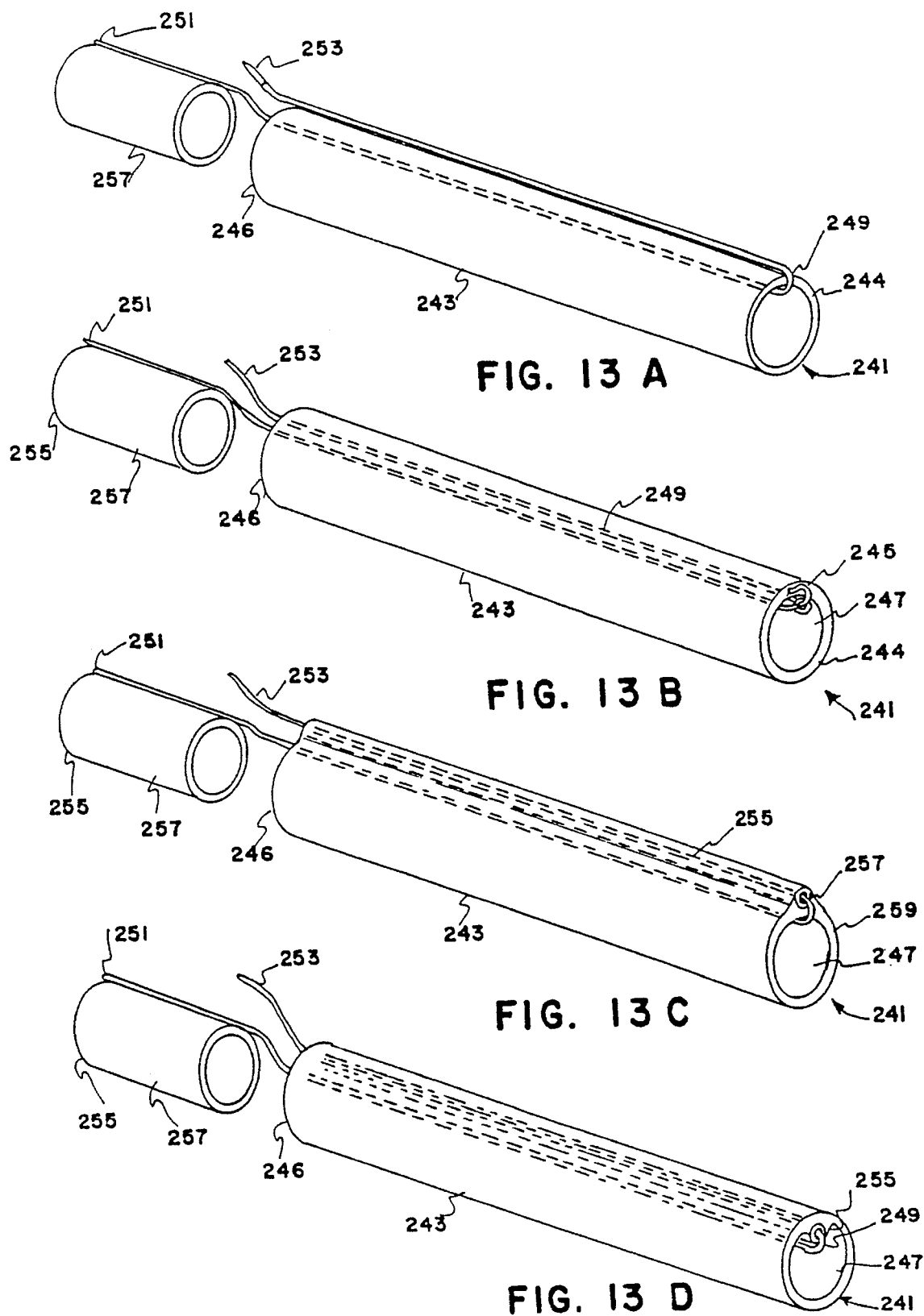

RETRACTION APPARATUS AND METHODS FOR ENDOSCOPIC SURGERY

This is a divisional of application Ser. No. 07/877,955, filed May 4, 1992 now U.S. Pat. No. 5,361,752, which is a continuation-in-part of Ser. No. 07/794,590 filed Nov. 19, 1991 now U.S. Pat. No. 5,309,896, which is a continuation-in-part of Ser. No. 07/706,781 filed May 29, 1991, now abandoned.

BACKGROUND OF THE INVENTION

Laparoscopy dates back to the turn of the 20th Century. Early laparoscopic techniques were used primarily for diagnostic purposes to view the internal organs, without the necessity of conventional surgery. Since the 1930s, laparoscopy has been used for sterilization and, more recently, for suturing hernias. U.S. Pat. Nos. 4,919,152 and 4,944,443 are concerned with techniques for suturing hernias. Another recent innovation is the use of laparoscopic surgery for removing the gallbladder.

U.S. patent application Ser. No. 706,781, the application of which this application is a continuation-in-part, describes an apparatus and method wherein the abdominal wall is lifted away from the underlying abdominal organs by an inflatable device which is introduced laparoscopically and, once in place, inflated to engage and lift an extensive area of the abdominal wall.

Even when such lifting techniques are used, it is still necessary to retract other organs to gain access to the organ or tissue to be treated or observed. In other procedures, to gain access to the organ or tissue to be treated or observed, the organ to be treated must be separated from tissue surrounding it. To obtain the necessary retraction, current laparoscopic procedures use several small metal or plastic retractors inserted though a plurality of incisions. Because such retractors have a relatively small surface area, they tend to damage and/or cause trauma to the retracted organs or tissue. Moreover, the requirement for a plurality of incisions to heal may delay the patient's recovery.

U.S. patent application Ser. No. 794,590 (the "prior application"), of which this application is also a continuation-in-part, describes a number of retraction devices that are introduced into the body in a collapsed condition and, once in place, are expanded by inflating a main inflatable chamber, to retract organs or tissues and to provide access to the organ or tissue being treated. The retraction devices described in the application provide a relatively large surface area to the organ or tissue being retracted so that retraction can take place with a minimal risk of damage to the retracted organ or tissue. These relatively large retraction devices include auxiliary means for maintaining their shape after inflation, such as an additional second inflatable chamber having a cage-like structure, or a spring cage arrangement. These auxiliary means enable retraction to be maintained after the main inflatable chamber has been deflated by cutting apertures in it to gain access through the retraction device to treat the organ or tissue being treated.

The retraction devices described in the prior application provide a significant improvement in providing access to the organ or tissue being treated during laparoscopic surgery. Nevertheless, such devices have problems. When an inflatable retraction device with an auxiliary cage structure providing a retraction effect equivalent to that of the main chamber is in its collapsed state, its envelope has a significant bulk. The bulk of a retraction device in its collapsed state will be called the "collapsed bulk" of the retraction device. An inflatable retraction device that has a large collapsed bulk is difficult to package in its collapsed state so that it can be inserted into the body through a narrow trocar tube (14 mm or less in diameter). Even when the package can be made small enough, it can be a tight fit in the trocar tube, and pushing such tight-fitting packages through the trocar tube is difficult. The package tends to buckle when pushed, and consequently jams in the tube. Less bulky retraction devices are therefore desirable.

It is also desirable to have a self-retracting endoscope to simplify endoscopic observation procedures.

SUMMARY OF THE INVENTION

In the following description, the word "organ" will be used to mean an organ or a tissue that is retracted by a retraction device. The word "treat" will be used to mean both treat and observe, and the word "treatment" will be used to mean both treatment and observation. The word "tissue" or the phrase "tissue to be treated" will both be used to mean the organ or the tissue that is treated through or inside a retraction device.

An inflatable retraction device according to the first aspect of the invention has a first inflatable chamber that retracts the organ when the first inflatable chamber is inflated to an expanded condition. The first inflatable chamber has a first envelope. The inflatable retraction device also includes a device that inflates the first inflatable chamber into an expanded condition while in place in the body. Inside the main inflatable chamber is a non-pressurized chamber that has a second envelope attached to part of the first envelope. The inflatable retraction device also has a second inflatable chamber attached to the non-pressurized chamber that expands the non-pressurized chamber into an expanded condition when the second inflatable chamber is inflated. Finally, the inflatable retraction device includes a device that inflates the second inflatable chamber.

The first inflatable chamber is inflated to retract the organ, and then remains inflated, and continues to provide retraction, throughout the treatment procedure.

The tissue is treated through an aperture in the part of the first envelope covered by the non-pressurized chamber. Instruments are passed from outside the body through a gas-tight port into the first inflatable chamber. From the first inflatable chamber, the instruments pass into the non-pressurized chamber through a port that seals around each instrument, and is self-sealing when the instrument is withdrawn. This maintains the first inflatable chamber in its inflated state. Alternatively, all or part of the envelope of the non-pressurized chamber can be made of an elastomeric material that seals around an instrument passed through it, and is self-sealing when the instrument is withdrawn. As a third alternative, instruments can be passed from outside the body through a duct connecting to the non-pressurized chamber.

The collapsed bulk of an inflatable retraction device according to the first aspect of the invention is less than that of an equivalently-sized inflatable retraction device of the types described in the prior application. This is because the volume the envelopes of the non-pressurized chamber and the second inflatable chamber is less than the volume of the envelope of the additional chamber of the types of inflatable retraction device previously described.

In a first method according to the invention of using an inflatable retraction device according to the first aspect of the invention to retract an organ inside the body to gain access to an adjacent tissue, the inflatable retraction device is placed in a collapsed state adjacent to the tissue. The first inflatable chamber is inflated into an expanded condition to retract the organ, and the second inflatable chamber is inflated to expand the non-pressurized chamber into an expanded condition.

In a second method according to the invention of using an inflatable retraction device according to the first aspect of the invention to retract an organ inside the body to gain access to an adjacent tissue, the inflatable retraction device in a collapsed condition is secured to an endoscope adjacent to the distal end of the endoscope. The distal end of the endoscope, together with the inflatable retraction device is inserted into the body and moved towards the tissue. The second inflatable chamber of the inflatable retraction device is at least partially inflated to expand the non-pressurized chamber into an expanded condition. This also expands the first inflatable chamber into a partially-expanded condition. The endoscope is manipulated while observing through the endoscope to place the at least partially expanded non-pressurized chamber adjacent to the tissue. Finally, the first inflatable chamber is inflated into a fully-expanded condition to retract the organ. The second method enables the part of the envelope of the first inflatable chamber covered by the non-pressurized chamber to be placed accurately relative to the organ to be treated.

An inflatable retraction device according to a second aspect of the invention has a main chamber that has an envelope of an elastomeric material. The main chamber is inflated while in place within the body to retract the organ into a retracted condition. The inflatable retraction device also includes a maintainer that maintains the organ in its retracted condition after the main chamber is deflated. Using an elastomeric material for the envelope of the main inflatable chamber enables the collapsed bulk of the main chamber, and hence the collapsed bulk of the inflatable retraction device as a whole, to be reduced compared with an inflatable retraction device having the same inflated size made from a substantially inelastic material.

In a first variation on the inflatable retraction device according to the second aspect of the invention, the maintainer is an additional inflatable chamber that has a cage-like structure and is independent of the main inflatable chamber. The main inflatable chamber is removed once the additional inflatable chamber is inflated and the tissue is treated using instruments passed through the maintainer. The additional inflatable chamber is preferably deployed on the outside of the main inflatable chamber, but can be deployed inside the main inflatable chamber.

In a second variation, the maintainer is a cage-like structure of a malleable metal or plastic deployed on the outside of the main inflatable chamber. The cage-like structure is expanded into an expanded condition by inflating the main inflatable chamber. Once the cage is in its expanded condition, the, main inflatable chamber can be deflated and removed, and the cage maintains the organ in its retracted condition.

In a method according to the invention of using an inflatable retraction device according to the second aspect of the invention, the maintainer and the main inflatable chamber are assembled together and packaged in a collapsed state. The maintainer and main inflatable chamber assembly is inserted into the body and placed adjacent to the organ. The main inflatable chamber is inflated to retract the organ into a retracted condition. The maintainer is expanded to maintain the organ in its retracted condition and the main inflatable chamber is deflated.

The collapsed bulk of the inflatable retraction devices described in the present application and in the prior application can be reduced by making the additional inflatable chamber smaller. If the additional inflatable chamber is to provide a given retracting force, it can only be made smaller if its strength is increased. In a method according to the third aspect of the invention, the strength of the additional inflatable chamber is increased by filling it with a solid instead of a fluid. In the method according to the third aspect of the invention, the main chamber of an inflatable retraction device is inflated. The additional inflatable chamber of the inflatable retraction device is then filled with a slurry comprising a particulate solid in a liquid. After the additional inflatable chamber has been filled with the slurry, the liquid component of the slurry is removed from the additional inflatable chamber, leaving the particulate solid behind. Finally, the particulate solid is compacted to form a rigid structure in the additional inflatable chamber. In the preferred embodiment, the particulate solid is compacted by evacuating the additional inflatable chamber. Alternative ways of compacting the particulate solid include heating and Cooling the solid.

A self-retracting endoscope according to the fourth aspect of the invention enables endoscopic observations to be carried out inside the body without the need for a separate retraction device. According to the fourth aspect of the invention, a self-retracting endoscope for observing a tissue inside the body includes an optical device for observing the tissue. The optical device has a substantially cylindrical structure, and a distal end that is inserted into the body through an incision. The self-retracting endoscope also includes a retractor that is expandable to retract organs adjacent to the tissue that would otherwise obstruct the view of the tissue. The retractor is attached to the optical device adjacent to the distal end of the optical device and is in a collapsed state when the distal end of the optical device is inserted into the body. The retractor is expanded once the distal end of the optical device is inside the body, adjacent to the tissue to be observed. In the preferred embodiment, the retractor is inflatable, and is expanded by inflating it.

The fifth aspect of the invention enables a substantially cylindrical object, such as an inflatable retraction device in its collapsed state, to be inserted into the body without buckling or jamming. An insertion tube according to the fifth aspect of the invention comprises an elongate tubular member having a bore. The bore receives the object, such as the collapsed inflatable retraction device, at its proximal end. A string passes from the proximal end to the distal end of the tubular member inside the bore and returns to the proximal end of the tubular member. The string passing inside the bore is capable of attachment to the proximal end of the object.

In a method according to the invention of using the insertion tube according to the fifth aspect of the invention, the string passing inside the bore is attached to the proximal end of the object, and the distal end of the object is inserted into the proximal end of the bore of the tubular member. The distal end of the tubular member is inserted into the body. The string returning to the proximal end of the tubular member is pulled to draw the object through the bore of the tubular member.

BRIEF DESCRIPTION OF THE DRAWINGS

FIG. 6A shows a packaged Type IIIA inflatable retraction device in its collapsed state inserted into the abdomen.

FIG. 6B shows the Type IIIA inflatable retraction device following inflation of the first inflatable chamber to retract the bowel, lift the liver, and gain access to the gall bladder.

FIG. 6C shows the Type IIIA inflatable retraction device following inflation of its second inflatable chamber. An endoscope and a cutting instrument has been inserted into the non-pressurized chamber to cut an aperture in the envelope of the main inflatable chamber through which to treat the gall bladder.

FIG. 7A is a cross sectional view of a partially inflated Type IIIA inflatable retraction device according to a first aspect of the invention being attached, to an endoscope prior to packaging the inflatable retraction device.

FIGS. 7B through 7E show cross sectional views of the abdomen including the bowel, the liver, and the gall bladder:

FIG. 7B shows a packaged Type IIIA inflatable retraction device attached in a collapsed state to an endoscope prior to insertion into the abdomen.

FIG. 7C shows the packaged Type IIIA inflatable retraction device attached in a collapsed state to an endo-scope after it has been inserted into the abdomen and the distal end of the endoscope has been placed adjacent to the gall bladder.

FIG. 7D shows the Type IIIA inflatable retraction device attached to an endoscope after the second inflatable chamber has been inflated, and the endoscope has been manipulated to align the treatment window in the second inflatable chamber with the gall bladder.

FIG. 7E shows the Type IIIA inflatable retraction device attached to an endoscope after the first inflatable chamber has been inflated to retract the bowel, lift the liver, and provide access to treat the gall bladder.

FIG. 9B shows a Type IVA inflatable retraction device after the main inflatable chamber has been inflated to retract the bowel and lift the liver to provide access to treat the gall bladder.

FIG. 9C shows the Type IVA inflatable retraction device after the maintainer has been inflated.

FIG. 9D shows the Type IVA inflatable retraction device after the main inflatable chamber has been deflated.

FIG. 9E shows the inflatable maintainer of a Type IVA inflatable retraction device in place in the abdomen maintaining the bowel in its retracted condition and the liver in its lifted condition after the inflatable retractor has been removed from the abdomen.

FIG. 10A is a perspective view of the maintainer.

FIG. 10B is a perspective view of the inflatable retractor.

FIG. 10C is a perspective view of the assembled Type IVB inflatable retraction device prior to insertion into the body.

FIG. 10D is a perspective view of the maintainer in its expanded condition following withdrawal of the inflatable retractor.

FIGS. 11A through 11D show a vertical cross sectional view of a Type IA inflatable retraction device to illustrate the high-strength inflation method according to the invention.

FIG. 11A shows the inflatable retraction device after its additional inflatable chamber has been filled with a slurry of a particulate solid in a liquid.

FIG. 11B shows the inflatable retraction device after the liquid component of the slurry has been removed its additional inflatable chamber.

FIG. 11C shows the inflatable retraction device after its additional inflatable chamber has been evacuated to consolidate the particulate solid.

FIG. 11D shows the inflatable retraction device fitted with an alternative provision for consolidating the particulate solid.

FIG. 12A is a perspective view of a self-retracting endoscope having an inflatable retractor comprising a stack of toroidal balloons. The inflatable retractor is shown in its expanded condition.

FIG. 12B is a cross sectional view of an alternative configuration of the inflatable retractor.

FIG. 12C is a perspective view of the self-retracting endoscope with its inflatable retractor in its collapsed condition.

FIG. 12D is a perspective view of a variation of the self-retracting endoscope having an inflatable retractor with the inflatable retractor in its collapsed condition. This variation has a substantially constant diameter circular cross section and is especially suitable for use in insufflated body cavities.

FIG. 12E is a cross sectional view of the abdomen showing the bowel, the liver, the gall bladder, and the self-retracting endoscope with an inflatable retractor retracting the liver to observe the gall bladder.

FIG. 12F is a perspective view of a self-retracting endoscope according to the invention having a mechanical retractor with the mechanical retractor in its collapsed condition.

FIG. 12G is a perspective view of the self-retracting endoscope having a mechanical retractor with the mechanical retractor in its expanded condition.

FIGS. 13A through 13D illustrate an insertion tube according to a fifth aspect of the invention:

FIG. 13A is a perspective view of a most basic insertion tube.

FIG. 13B is a perspective view of a less basic insertion tube having an eyelet.

FIG. 13C is a perspective view of an improved version of the insertion tube having an external narrow bore tube.

FIG. 13D is a perspective view of an improved version of the insertion tube having an internal narrow bore tube.

DETAILED DESCRIPTION OF THE INVENTION

1. TYPE III INFLATABLE RETRACTION DEVICES

(a) Type IIIA Inflatable Retraction Device

Figure 1:
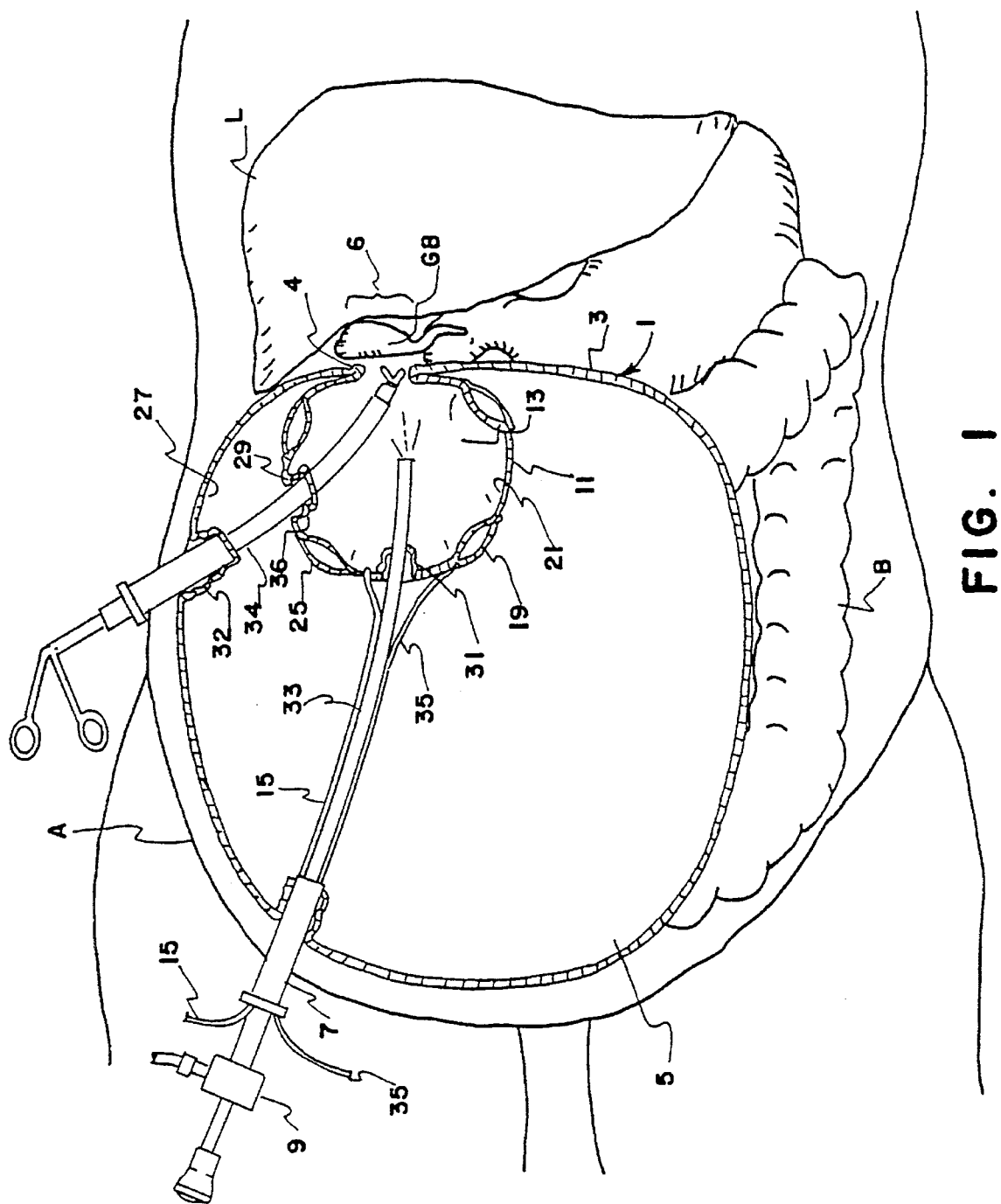
FIG. 1 shows a cross sectional view of a Type IIIA inflatable retraction device according to a first aspect of the invention in its inflated condition in the abdomen.

FIG. 1 shows a vertical cross sectional view of a retraction device according to the first aspect of the invention. This type of retraction device has a second inflatable chamber that expands a non-pressurized chamber into an expanded condition when the second inflatable chamber is inflated, and will be designated as a Type III retraction device. The Type III inflatable retraction device shown in FIG. 1 with a segmented non-pressurized chamber will be designated as a Type IIIA inflatable retraction device. The inflatable retraction device 1 is shown in its inflated condition. The inflatable retraction device 1 comprises a first envelope 3 enclosing a first inflatable chamber 5. Inside the first inflatable chamber 5 is the non-pressurized chamber 13, which is maintained in an expanded condition by the second inflatable chamber 25.

The inflatable retraction device 1 is shown being used in the abdomen A to retract the bowel B, lift the liver L, and provide access to treat the gall bladder GB. After the inflatable retraction device 1 has been deployed, an aperture 4 is cut in the treatment window 6 to gain access to the gall bladder GB. The treatment window is the part of the first envelope 3 covered by the non-pressurized chamber 13. Alternatively, the inflatable retraction device 1 may be supplied with the aperture 4 already cut in the treatment window 6. The non-pressurized chamber 13, supported by the second inflatable chamber 25, isolates the aperture 4 from the first inflatable chamber 5. This enables the first inflatable chamber to remain inflated and to continue to provide retraction of the bowel B. Because of the aperture 4, the interior of the non-pressurized chamber 13 is at atmospheric pressure, or, if the abdomen A is insufflated, at the ambient pressure of the abdomen.

Instruments, such as the endoscope 33, pass into the first inflatable chamber 5 through the gas-tight port 9 on the first inflation tube 7, and thence through the gas-tight port 31 into the non-pressurized chamber 13 to observe or to treat the gall bladder GB. Additionally or alternatively, instruments, such as the forceps 34, can pass through the gas-tight port 32 into the first inflatable chamber, and thence through a gas-tight port, such as the port 36, into the non-pressurized chamber. The gas-tight ports 9, 31, 32, and 36 enable the first inflatable chamber to remain inflated.

The first envelope 3 of the inflatable retraction device 1 can be made of a relatively inelastic and tough film of a plastic such as Mylar® or polyethylene. The preferred relatively inelastic material is a polyethylene and nylon composite with a thickness in the range from 0.5 to 5 mils (13 to 130 microns). Alternatively, the first envelope can be made of an elastomeric material such as latex, polyurethane, or silicone rubber with a thickness in the range from 0.5 to 5 mils (13 to 130 microns).

The proximal end of a first inflation tube 7 is sealed into the first envelope 3. The first inflation tube 7 allows an inflation gas to pass into and out of the first inflatable chamber 5. The inflation gas is typically air, nitrogen or carbon dioxide, although other suitable gases may be used. Typical inflation gas pressures are in the range 0.2 to 0.4 pounds per square inch (psi) (0.14 to 0.28 kPa), the preferred pressure being 0.3 psi (0.21 kPa). The first inflation tube 7 is provided with a gas-tight port 9 on its distal end, through which endoscopes and/or surgical instruments can be passed into the first inflatable chamber 5. The port 9 allows the inflation pressure of the first inflatable chamber 5 to be maintained when surgical instruments are passed through it.

The first envelope 3 of the Type IIIA inflatable retraction device can be a polyhedral structure constructed from two segmented, substantially flat pieces of material, which gives the inflatable retraction device a substantially polyhedral shape. Alternatively, the inflatable retraction device can be constructed from one or more curved pieces of plastic film, which gives the inflatable retraction device a substantially spherical, spheroidal, or ellipsoidal shape, as shown in FIG. 1.

The size of inflatable retraction devices according to the invention can range from about 2" (50 mm) wide by about 0.5" (12 mm) high, for use inside the pericardium, to 10"–14" (250–350 mm) wide by 4"–8" (100–200 mm) high, for use in the abdominal cavity. The size of inflatable retraction device required for a given application depends on the application and the size of the patient.

The second envelope 11, which bounds the non-pressurized chamber 13, is preferably made from substantially the same thickness of the same material as the first envelope 3. However, in some applications it may be advantageous make the second envelope 11 using a different thickness of the same material as the first envelope, or using the same or a different thickness of a different material.

The second envelope 11 can be a polyhedral structure constructed from two segmented, substantially flat pieces of material, with the edges of the segments joined to give the non-pressurized chamber 13 a substantially polyhedral shape. Alternatively, the non-pressurized chamber 13 can be constructed from one or more curved pieces of material, which gives the non-pressurized chamber 13 a substantially spherical, spheroidal, or ellipsoidal shape. This form of construction is particularly appropriate if an elastomeric material is used for the second envelope 11.

Despite its name, the non-pressurized chamber may be briefly inflated to assist in expanding it from its collapsed condition to its expanded condition against the pressure exerted on it by the first inflatable chamber 3. If the non-pressurized chamber is to be inflated, it is provided with the second inflation tube 15.

Figure 2A:
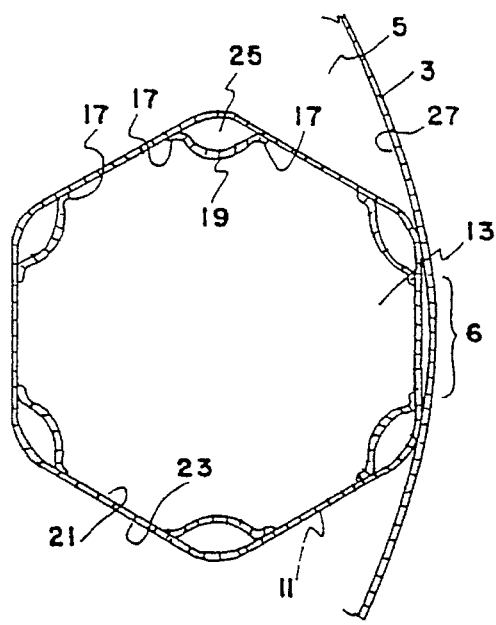
FIG. 2A is a cross sectional view showing details of the non-pressurized chamber and the second inflatable chamber of a Type IIIA inflatable retraction device according to a first aspect of the invention.

The periphery 17 of the third envelope 19 is attached to the second envelope 11. This is shown in detail in FIG. 2A. The third envelope is preferably attached to the inside surface 21 of the second envelope. The third envelope 19 has a segmented shape such that, when its periphery 17 is attached to the second envelope 11, and the second inflatable chamber 25 formed between the second envelope 11 and the third envelope 19 is inflated, the second inflatable chamber 25 forms a cage structure inside or outside the non-pressurized chamber 13. FIG. 2A shows the second inflatable chamber 25 formed inside the non-pressurized chamber 13. Alternatively, the third envelope may be attached to the outside surface 23 of the second envelope as shown in FIG. 1. When the non-pressurized chamber 13 is a polyhedral structure, the cage structure of the second inflatable chamber is preferably formed on the faces of the polyhedron.

The third inflation tube 35 allows an inflation gas to pass into and out of the second inflatable chamber 25. The inflation gas is typically air, nitrogen or carbon dioxide, although other suitable gases may be used. Typical inflation gas pressures are in the range 2 to 5 psi (1.4 to 3.5 kPa), the preferred pressure being 3.5 psi (2.4 kPa). The inflation gas pressure in the second inflatable chamber 25 is considerably higher than that in the first inflatable chamber 5 to enable the second inflatable chamber to exert sufficient force to support the non-pressurized chamber 13 against the pressure exerted on it by the inflation pressure in the first inflatable chamber.

In an embodiment of the Type IIIA retraction device designed for use in an insufflated body cavity, the second inflation tube 15, if fitted, and the third inflation tube 35 are contained within the first inflation tube 7, a shown in FIG. 1. The outer wall of the first inflation tube 7 forms a gas-tight seal with the trocar tube or introducer sleeve through which the first inflation tube passes into the body. Alternatively, the three inflation tubes can all be mounted in a tube sheath that forms a gas-tight seal with the trocar tube or introducer sleeve through which the tube sheath passes into the body.

Figure 3A:
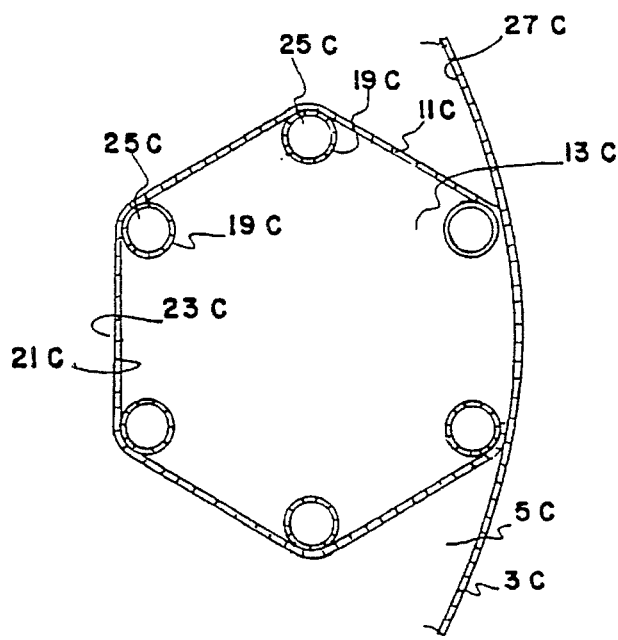
FIG. 3A is a cross sectional view showing the non-pressurized chamber and the second inflatable chamber of a Type IIIA inflatable retraction device according to a first aspect of the invention in which the second inflatable chamber is inside the non-pressurized chamber and has its own envelope.
Figure 3B:
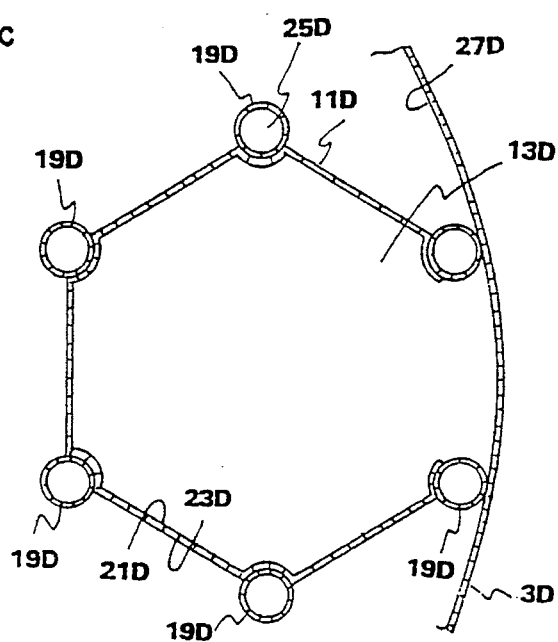
FIG. 3B is a cross sectional view showing the non-pressurized chamber and the second inflatable chamber of a Type IIIA inflatable retraction device according to a first aspect of the invention in which the second inflatable chamber is outside the non-pressurized chamber and has its own envelope.

FIG. 2A shows the second inflatable chamber 25 formed between part of the second envelope 11 and the third envelope 19. FIGS. 3A and 3B illustrate an alternative embodiment in which the third envelope 19C is formed into a geodesic tubular structure that provides the envelope for the second inflatable chamber 25C exclusively. In FIG. 3A, the second inflatable chamber 25C is formed inside the non-pressurized chamber 13C. In this configuration, there is no need to attach the second inflatable chamber to the inside surface 21C of the second envelope 11C. In FIG. 3B, the second inflatable chamber 19D is attached to the outside surface 23D of the second envelope 11D.

Although providing the second inflatable chamber with its own envelope, as shown in FIG. 3C, increases the volume of material used for the third envelope 19C, it enables a considerably thinner material to be used for the second envelope 11C and thus gives in a overall reduction in the collapsed bulk of the: inflatable retraction device. A thinner material can be used for the second envelope because the second envelope is subject only to the inflation pressure of the first inflatable chamber 5C, and is not subject to the much higher inflation pressure of the second inflatable chamber 25C. This alternative form of construction is especially preferred when an elastomeric material is used for at least part of the second envelope 11C. The foregoing also applies to the embodiment shown in FIG. 3D.

Figure 2B:
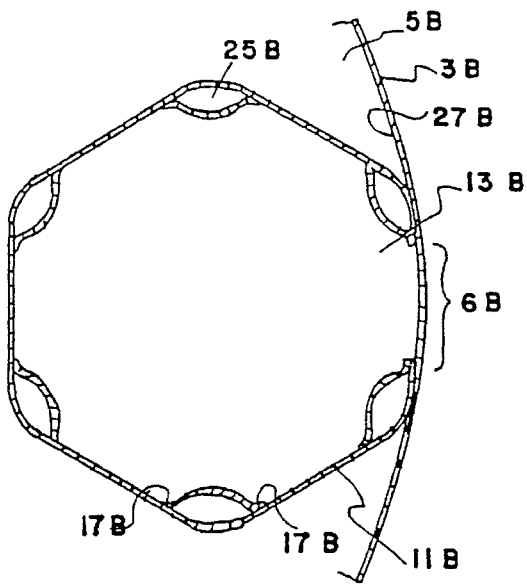
FIG. 2B is a cross sectional view showing a version of the non-pressurized chamber in which the part of its envelope contacting the envelope of the first inflatable chamber is removed.

Part of the outside surface 23 of the second envelope is attached to the inside surface 27 of the first envelope 3, as shown in FIG. 2A. The part of the first envelope covered by the non-pressurized chamber 13 provides the treatment window 6. The second envelope 11 may be left intact over the treatment window 6, in which case there is a double thickness of material covering the treatment window 6, as shown in FIG. 2A. Alternatively, as shown in FIG. 2B, part of the second envelope lIB may be removed, such as one face of the polyhedron if the non-pressurized chamber is a polyhedron, to avoid a double thickness of material over the treatment window 6B. In either case, the second envelope must be attached to the first envelope to form a gas-tight seal between them.

The pans of the second envelope 11 not obstructed by the second inflatable chamber 25 provide a plurality of windows 29, as shown in FIG. 1. At least one of the windows is fitted with a port 31 which enables a surgical instrument to be passed from the first inflatable chamber 5 into the non-pressurized chamber 13. When an instrument, such as the endoscope 33, is passed through the port 31, the port forms a gas-tight seal with the instrument. When the instrument is withdrawn from the port 31, the port once more forms a gas-tight seal with itself. The port 31 provides a gas-tight access from the first inflatable chamber 5 to the non-pressurized chamber 13 that maintains the inflation pressure in the first inflatable chamber. The port 31 preferably includes a window of an elastomeric material such as latex, polyurethane, or silicone rubber. A slit may be pre-cut in the window to make it easier to pass instruments through the window.

As an alternative to the port 31 shown in FIG. 1, an instrument may be passed directly through the window 29 if at least the part of the second envelope forming the window 29 is of an elastomeric material.

Figure 4:
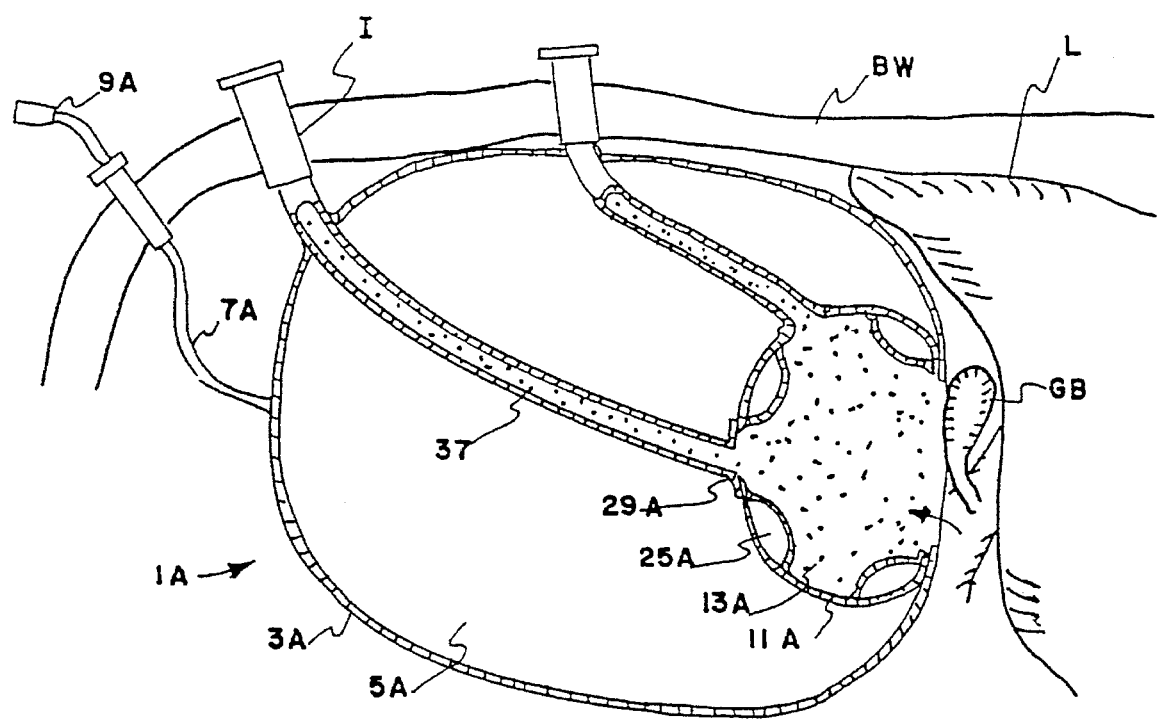
FIG. 4 is a cross sectional view of a Type IIIA inflatable retraction device according to a first aspect of the invention in its inflated condition in the abdomen and having ducts through which instruments can be inserted into the non-pressurized chamber from outside the inflatable retraction device.

FIG. 4 shows an alternative to using some form of port between the first inflatable chamber and the non-pressurized chamber to allow a surgical instrument to be passed into the non-pressurized chamber. In FIG. 4, features similar to those in FIG. 1 are indicated by the same reference number with the letter "A" added. The inflatable retraction device 1A is provided with a duct 37, which is a tube of an inelastic plastic material similar to that which may be used for the first envelope 3A. The duct 37 is sealed into one of the windows 29A in the second envelope 11A, passes proximally through the first inflatable chamber 5A, is settled through the first envelope 3A, and extends beyond the first envelope as shown.

After the inflatable retraction device 1A has been deployed, an incision I is made in the abdominal wall BW, and the proximal end of the duct 37 is brought out through the incision I. The duct 37 provides a passage at atmospheric pressure through which a surgical instrument can be passed from outside the body directly into the non-pressurized chamber 13A, and thence to the gall bladder GB. This arrangement provides better feel for the surgeon because movement of the instrument is not restricted by the two gas-tight ports 9 and 31 (FIG. 1). However, the duct 37 must be fitted with a gas-tight port if the inflatable retraction device 1A is used in an insufflated body cavity to prevent insufflation gas from leaking out through the duct. Inflatable retraction devices according to the invention may have both ports and ducts.

(b) Type IIIB Inflatable Retraction Device

Figure 5:
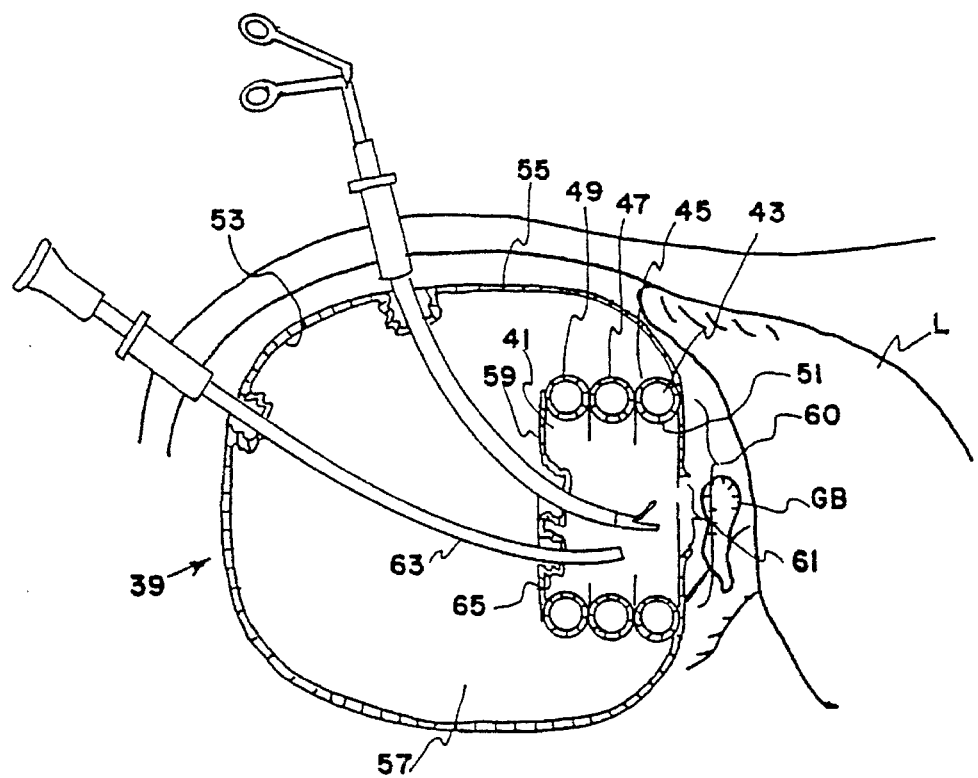
FIG. 5 is a cross sectional view of a Type IIIB inflatable retraction device according to a first aspect of the invention in its inflated condition in the abdomen.

FIG. 5 shows the Type IIIB inflatable retraction device 39, which is a variation on the Type IIIA inflatable retraction device having a different structure for the non-pressurized chamber and the second inflatable chamber. In FIG. 5, the first inflatable chamber 57 is substantially the same as the first inflatable chamber 5 shown in FIG. 1 and will therefore not be described further. The polyhedral or substantially spherical or spheroidal non-pressurized chamber 13 of FIG. 1 is replaced by a substantially cylindrical non-pressurized chamber 41.

The part of the first envelope 55 of the first inflatable chamber covered by the non-pressurized chamber 41 provides a treatment window 60 in which an aperture 61 can be cut to gain access to the tissue being treated, in this example, the gall bladder GB. The non-pressurized chamber 41 enables the first inflatable chamber 57 to remain in its inflated state, and to continue to provide retraction, despite the presence of an aperture 61 in the treatment window 60. The non-pressurized chamber 41 is enclosed by part of the third envelope 51, the treatment window 60, and the diaphragm 59. The diaphragm is preferably made of an elastomeric material such as latex, polyurethane or silicone rubber.

The second inflatable chamber 43 comprises a stack of toroidal balloons which is enclosed by the third envelope 51. A stack of three toroidal balloons 45, 47, and 49 is shown: a greater or lesser number of toroidal balloons can be used, depending on the application. The second inflatable chamber 43 is attached to the inner surface 53 of the first envelope 55 of the first inflatable chamber 57.

The third envelope 51 of the inflatable retraction device 39 is made of a relatively inelastic and tough film of a plastic such as Mylar®, polyethylene, or polyurethane. The preferred material for the third envelope 51 is a polyethylene and nylon composite. The thickness of the third envelope 51 is typically from 0.5 to 5 mils (13 to 130 microns).

The non-pressurized chamber 41 can be briefly inflated by means of a second inflation tube (not shown) to assist its initial expansion, as already described. The second inflatable chamber 43 has a third inflation tube (not shown) sealed into it. If a stack of toroidal balloons 45, 47, and 49 is used for the second inflatable chamber 43, as shown in FIG. 5, they may simply be interconnected, and a single third inflation tube used. Alternatively, a third inflation tube may be fitted to each toroidal balloon to allow the height of the non-pressurized chamber to be adjusted by selectively inflating the balloons in the stack. In a further alternative, a single third inflation tube can feed a manifold leading to each balloon through a non-return valve. All balloons in the stack are inflated initially. The height of the non-pressurized chamber 41 can then be reduced by puncturing one or more of the balloons.

The diaphragm 59 provides one large window through which an instrument, such as the endoscope 63, may be passed from the first inflatable chamber 57 into the non-pressurized chamber 41. Gas-tight seals must be provided around such instruments. Using an elastomeric material for the diaphragm 59, or using a substantially inelastic material for the diaphragm 59 and fitting a port 65, similar to the port 31 in FIG. 1 will provide suitable gas-tight seals. Alternatively, a duct, similar to the duct 37 of FIG. 4, can be used in the retraction device 39 of FIG. 5, preferably attached to the diaphragm 59, to provide a passage at atmospheric pressure from outside the body through the first inflatable chamber to the non-pressurized chamber 41.

(c) First Method of Use

In the following description, the word "organ" will be used to mean an organ or a tissue that is retracted by the inflatable retraction device. The word "treat" will be used to mean both treat and observe, and the word "treatment" will be used to mean both treatment and observation. The word "tissue" or the phrase "tissue to be treated" will both be used to mean the organ or the tissue that is treated through or inside the retraction device.

Figure 6A:
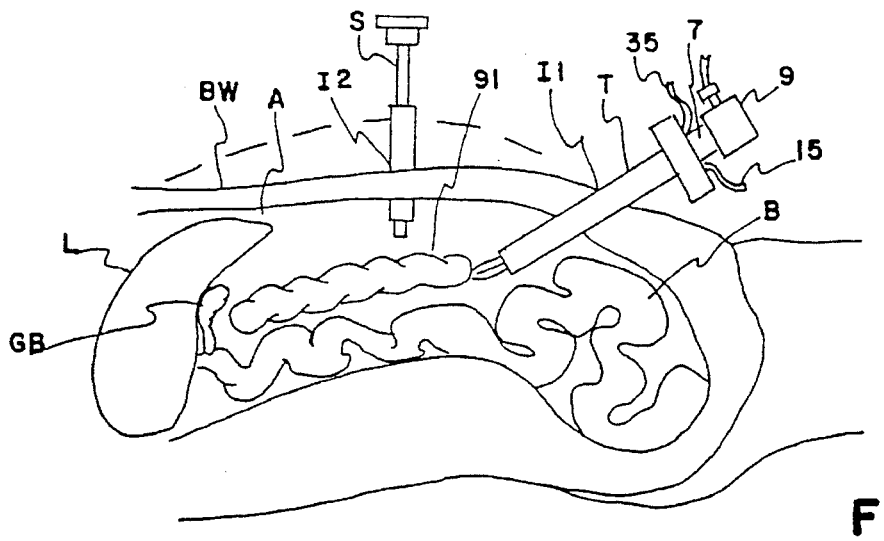
FIGS. 6A through 6C show cross sectional views of the abdomen including the bowel, the liver, and the gall bladder to illustrate a first method according to the invention of using a type IIIA or a type IIIB inflatable retraction device according to the invention to retract the bowel and lift the liver to gain access to treat the gall bladder.
Figure 6B:
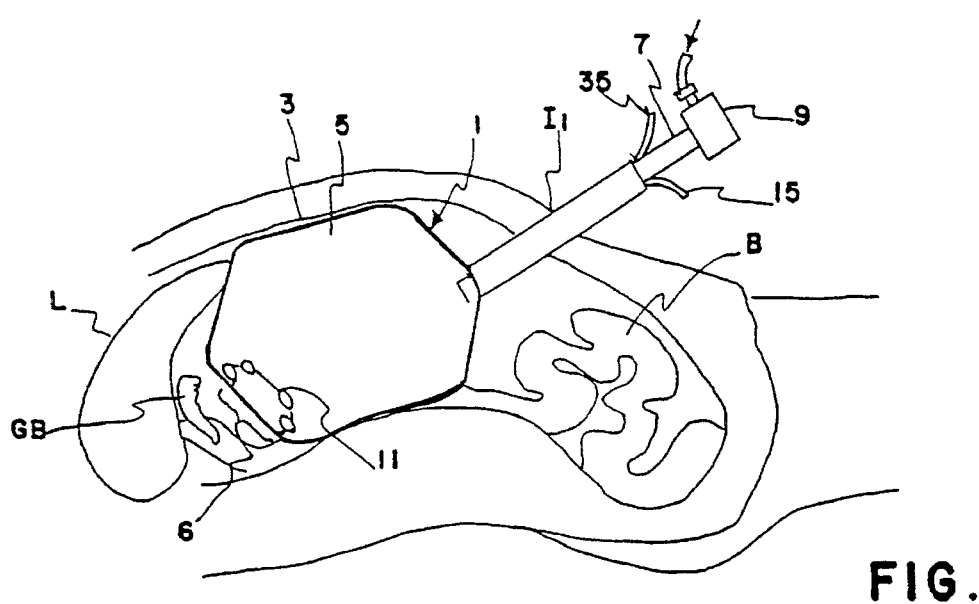
Figure 6C:
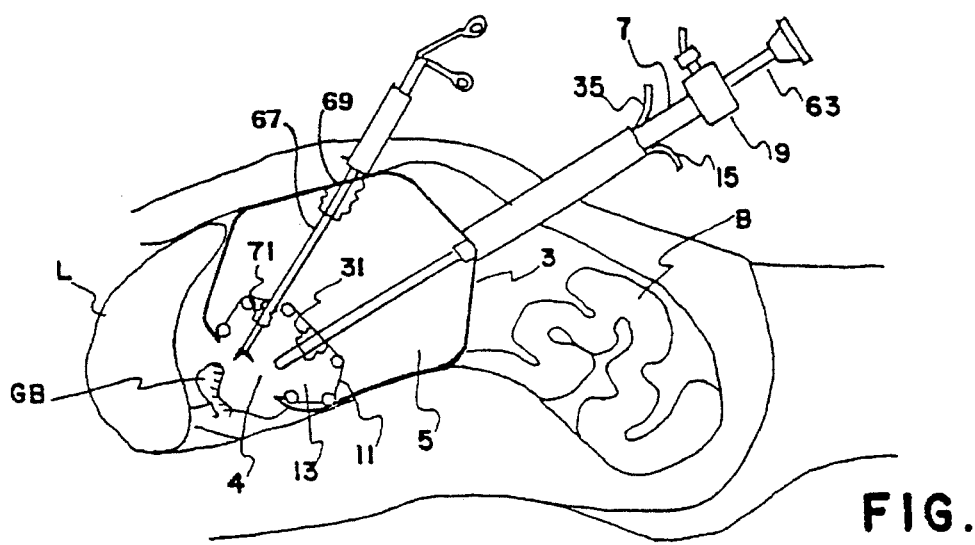

FIGS. 6A through 6C show cross sectional elevational views of the abdomen A to illustrate the method by which a Type IIIA inflatable retraction device according to the invention is used in the body to retract an organ within the body to gain access to treat a tissue. In the method illustrated in FIGS. 6A through 6C, the inflatable retraction device is inserted into the abdomen A and is used to retract an organ, the bowel B, to gain access to treat a tissue, the gall bladder GB. The inflatable retraction device also lifts the liver L. The method according to the invention can also be used to deploy a Type IIIA inflatable retraction device in other parts of the body, and to deploy a Type IIIB inflatable retraction device in the same or in other parts of the body.

The inflatable retraction device 1 is supplied in a collapsed state 91, as shown in FIG. 6A, in which it is tightly packaged in a configuration that makes it essentially a linear extension of the first inflation tube 7. The collapsed inflatable retraction device is introduced into the body by pushing it through a suitable introducer sleeve or trocar tube T that has been inserted through a suitable incision I1 in the body wall BW. Alternatively, an introducer tube according to the fourth aspect of the invention, to be described below, can be used. The trocar tube T is oriented so that, when the collapsed inflatable retraction device 91 is ejected from the trocar tube T, it is located adjacent to the organ as shown. The location of the collapsed retraction device is checked by an endoscope S inserted into the body through a second incision I2. Once the collapsed retraction device 91 is correctly located, it is released from its packaging.

The first inflation tube 7 is connected to a source of inflation gas (not shown) and the gas supply is slowly turned on to inflate the first inflatable chamber 5. The first inflatable chamber slowly expands, as shown in FIG. 6B, progressively retracting the bowel B and lifting the liver L as its size increases. Throughout the expansion process, the first inflatable chamber 5 presents a relatively large surface area to the bowel and the liver, and thus retracts the bowel and lifts the liver gently, progressively, and without trauma. Although the first inflatable chamber 5 retracts the bowel and lifts the liver gently, it is capable of exerting the force necessary to effect the retraction of the bowel and the lifting of the liver.

Once the first inflatable chamber 5 has reached its fully-inflated condition, the position of the treatment window 6 relative to the tissue is checked by observation through the endoscope S and/or an endoscope (not shown) inserted into the first inflatable chamber 5 through the first inflation tube 7 and the gas-tight port 9. The tissue to be treated must be substantially centered in the treatment window 6. If the inflatable retraction device 1 is supplied with the aperture 4 already cut in the treatment window 6, the aperture 4 must be substantially centered on the tissue to be treated, i.e., the gall bladder in this example. If the inflatable retraction device 1 is not correctly positioned, the inflation gas pressure is reduced slightly to partially deflate the first inflatable chamber and the inflatable retraction device 1 is manipulated to correct its orientation. The first inflatable chamber 5 is then reinflated.

The non-pressurized chamber 13 is next expanded. The source of inflation gas (not shown) is connected to the second inflation tube 15 and the gas supply is slowly turned on to inflate the non-pressurized chamber 13 to its fully extended condition. An inflation pressure slightly greater than that used to inflate the first inflatable chamber 5 is used. The second inflation tube is clamped, and the source of inflation gas is transferred to the third inflation tube 35. The gas supply is slowly turned on to inflate the second inflatable chamber 25. An inflation pressure approximately ten times that used to inflate the first inflatable chamber is used. Once the second inflatable chamber is fully inflated, inflation pressure is released from the non-pressurized chamber 13.

Temporarily inflating the non-pressurized chamber 13 before inflating the second inflatable chamber 25 is the preferred way of expanding the non-pressurized chamber. Inflating the non-pressurized chamber first makes it easier to inflate the second inflatable chamber, and enables the size of the second inflatable chamber to be reduced. More force is required to expand the., non-pressurized chamber 13 from a collapsed condition against the inflation pressure of the first inflatable chamber 5 than to maintain the non-pressurized chamber in an already-expanded condition against the inflation pressure of the first inflatable chamber. However, inflating the non-pressurized chamber is not essential, and the step of inflating the non-pressurized chamber can be omitted if desired. Inflation cannot be used to help expand the non-pressurized chamber if the inflatable retraction device 1 is supplied with the aperture 4 already cut in the treatment window 6.

If the aperture 4 is already cut in the treatment window 6, treatment of the tissue can begin using one or more instruments passed through the gas-tight port 9 and the first inflation tube 7 into the first inflatable chamber 5 and thence through the port 31 into the non-pressurized chamber 13.

If the aperture 4 is to be cut in the treatment window 6, an endoscope 63 is passed through the port 9 and the first inflation tube 7 into the first inflatable chamber 5, and from the first inflatable chamber 5 through the gas-tight port 31 into the non-pressurized chamber 13. A cutting instrument 67 is then passed into the first inflatable chamber through the gas-tight port 69, and from the first inflatable chamber to the non-pressurized chamber through the gas-tight port 71. The cutting instrument is then used to make a cut in, and possibly to remove part of, the treatment window 6 to provide the aperture 4. If the second envelope 11 covers the part of the first envelope cut or removed (see FIG. 2A), this part of the second envelope must also be cut or removed.

The tissue to be treated is treated using instruments passed through ports such as the port 31 into the non-pressurized chamber 13. The instruments are then passed out of the non-pressurized chamber through the aperture 4 to treat the tissue. Alternatively, the tissue can be pulled into the non-pressurized chamber through the aperture 4 and the treatment can be carried out inside the non-pressurized chamber. The edges of the aperture 4 form a seal against the tissue and keep blood, debris, etc. safely inside the non-pressurized chamber, from whence they can easily be removed.

If the inflatable retraction device is of the configuration shown in FIG. 4, and has a duct 37 instead of, or in addition to, the gas-tight port 31, the duct 37 is used to pass the endoscope 63 and the cutting instrument 67 into the non-pressurized chamber in the method described above. Alternatively, both ducts and ports can be used.

The need for extensive manipulation of the inflatable retraction device 1 to center the treatment window 6 on the tissue being treated can be reduced by providing further non-pressurized chambers attached to the first envelope 3. Each non-pressurized chamber provides a differently-oriented treatment window and has its own second inflatable chamber. After the first inflatable chamber 5 is inflated, the one or more non-pressurized chambers that provide the most favourably aligned treatment windows relative to the tissue being treated are expanded as described above, and are used to provide access to treat the tissue.

(d) Second Method of Use

FIGS. 7B through 7E show cross sectional elevational views of the abdomen A to illustrate the second method according to the invention of using a Type IIIA inflatable retraction device according to the invention to retract the bowel B and lift the liver L to gain access to the gall bladder GB, as in the first method described above. The same method can be used with a Type IIIB inflatable retraction device, and the method can be adapted for use in connection with treating other tissues.

The first method of using a Type III inflatable retraction device involves a tedious process to align the treatment window 6 with the tissue to be treated. The second method of using a Type III inflatable retraction device simplifies aligning the inflatable retraction device 1 relative to the tissue to be treated.

Figure 7A:
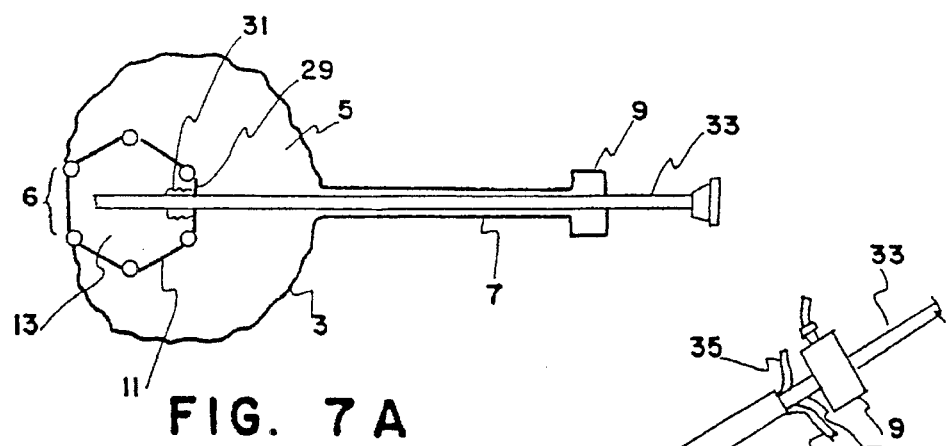
FIGS. 7A through 7E illustrate a second method according to the invention of using a type IIIA or a type IIIB inflatable retraction device according to the invention to retract an organ.

Before the inflatable retraction device 1 is inserted into the body, both the first inflatable chamber 5 and the second inflatable chamber 13 are partially inflated, and the inflatable retraction device is assembled with the endoscope 33 as shown in FIG. 7A. The distal end of the endoscope 33 is inserted into the first inflatable chamber 5 through the first inflation tube 7 and the gas-tight port 9. The distal end of the endoscope 33 is pushed through the gas-tight port 31 into the non-pressurized chamber 13 and is centered in the treatment window 6. Alternatively, a gas-tight port specifically designed to seal with the endoscope 33 can be incorporated into the second envelope 11 to receive the endoscope. The first and second inflatable chambers are then collapsed by evacuating them.

Figure 7B:
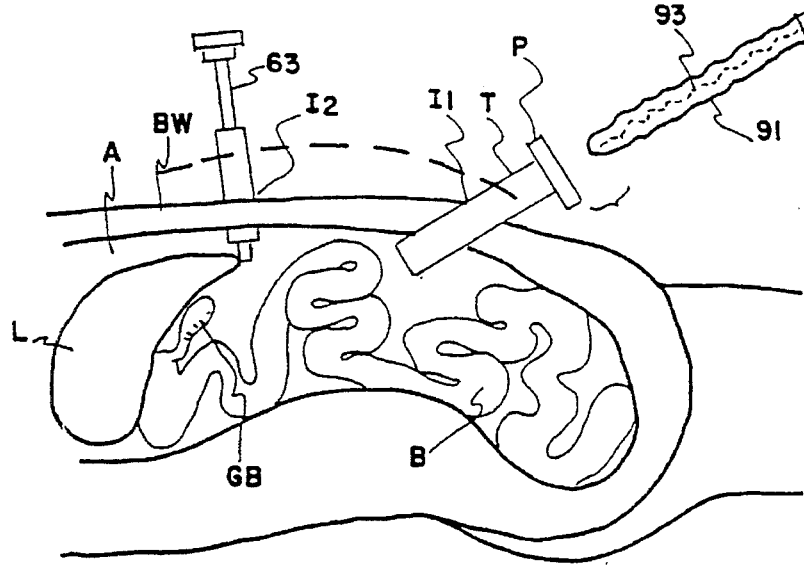

The inflatable retraction device is then wrapped around the shaft of the endoscope 33, adjacent to the distal end of the endoscope as shown in FIG. 7B. If an aperture is already cut in the treatment window 6, the tip of the endoscope is exposed. Otherwise, the tip of the endoscope is covered by at least a layer of the first envelope 3, as shown in FIG. 7B. The collapsed inflatable retraction device 91 is held in position by detachable lacing 93. Alternatively, the collapsed inflatable retraction device can be held in position by a sleeve with detachable lacing, by a sleeve with a tear strip, or by another suitable method. The packaged assembly has an overall diameter of about 11 mm, which enables the package to fit through a 12 mm trocar tube.

Figure 7C:
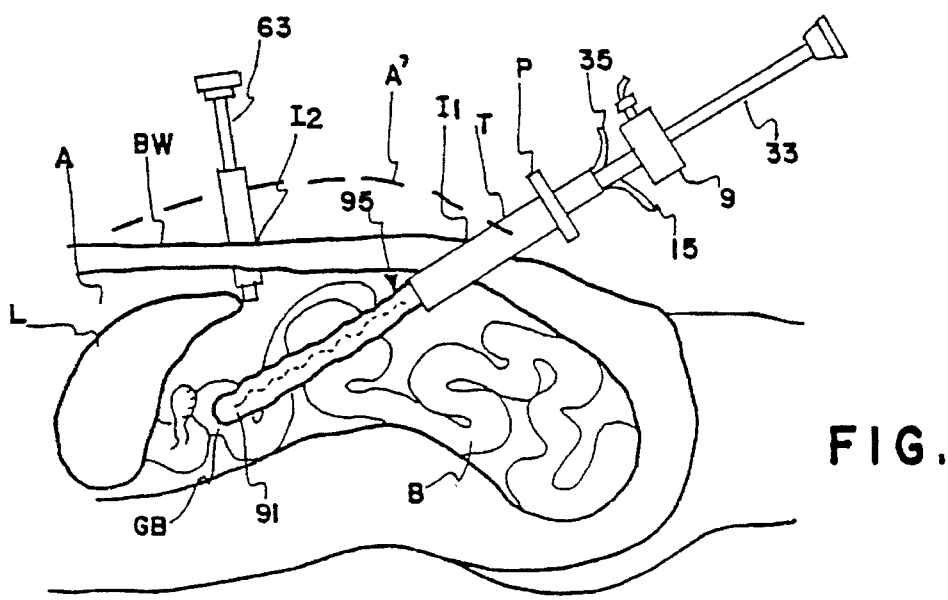

Before the assembly is inserted into the body, it may be necessary to insufflate the abdomen A temporarily to create space in which to maneuver the distal end of the endoscope/retractor assembly 95 into proximity with the tissue to be treated. Insufflation techniques are known and will not be described. The insufflated condition is indicated by the broken line marked A' in FIG. 7B. An incision I1 is made in the abdominal wall BW and a trocar tube T is driven through the wall. The endoscope/retractor assembly 95 is inserted into the abdomen through the trocar tube (and a gas-tight port P on the trocar tube if the body cavity is insufflated). While viewing through the endoscope 33, and, if desired, through an additional endoscope 63 inserted into the abdomen in the vicinity of the gall bladder GB through an additional incision I2, the endoscope 33 is manipulated to bring its distal end close to the gall bladder GB, as shown in FIG. 7C.

Figure 7D:
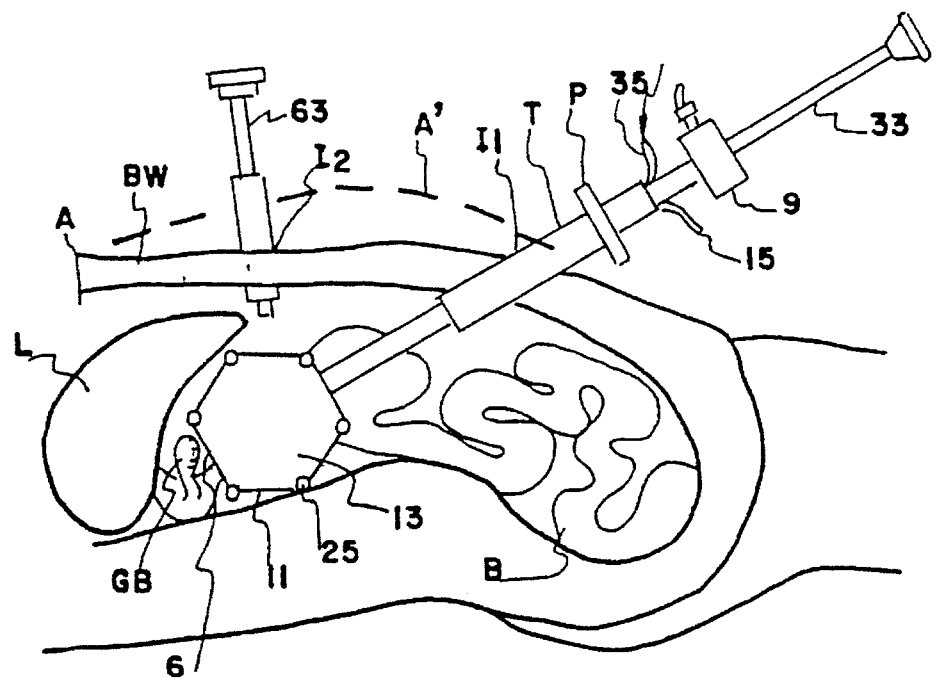

The inflatable retraction device 1 is then released from its packaging and the non-pressurized chamber 13 is expanded into its expanded condition as shown in FIG. 7D. If an aperture is not already cut in the treatment window 6, the non-pressurized chamber is preferably expanded by temporarily inflating it using the second inflation tube 15. The second inflatable chamber 25 is then inflated with inflation gas through the third inflation tube 35. If the aperture is already cut, or if the second inflation tube is not provided, the non-pressurized chamber is expanded by inflating the second inflation chamber 25 with inflation gas through the third inflation tube 35. With the non-pressurized chamber expanded, the endoscope 33 is then manipulated, while observing at least through the endoscope 33, to center the treatment window 6 on the tissue to be treated, i.e., the gall bladder GB. The endoscope 33 is then clamped in position to hold the non-pressurized chamber in its correct location relative to the gall bladder when the first inflatable chamber is inflated.

Figure 7E:
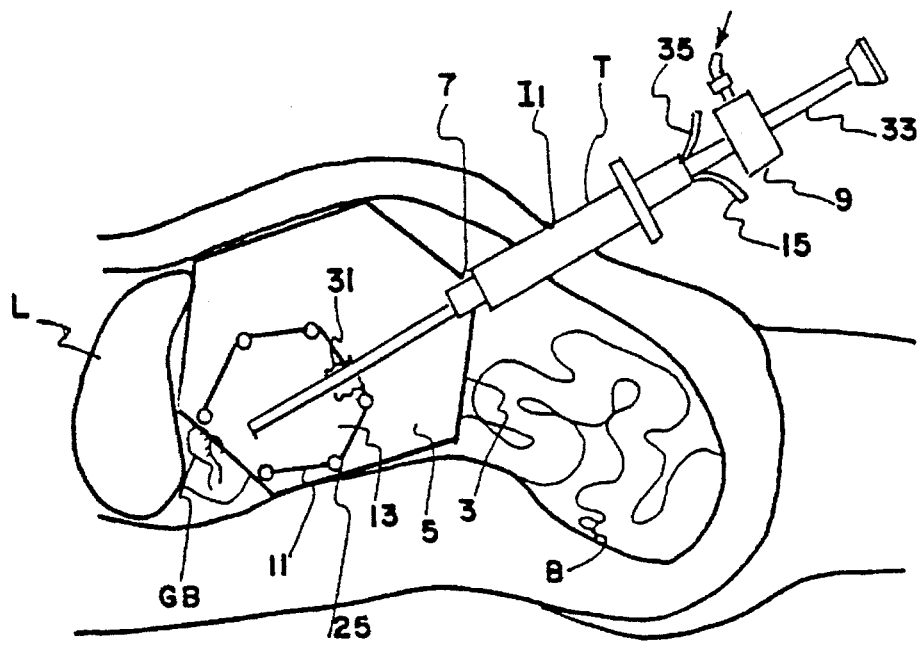

The first inflation tube 7 is connected to the supply of inflation gas (not shown) and inflation pressure is slowly increased to expand the first inflatable chamber 5. The expanding first inflatable chamber gently retracts the bowel B, lifts the liver L, and provides a working space in front of the gall bladder GB, as shown in FIG. 7E.

After the inflatable retraction device has been deployed according to the method just described, instruments are passed into the first inflatable chamber 5 and thence into the non-pressurized chamber 13 to treat the gall bladder as described above. The method described above can also readily be adapted to deploy an inflatable retraction device with ducts, as shown in FIG. 4.

2. TYPE IV INFLATABLE RETRACTION DEVICES

Figure 8A:
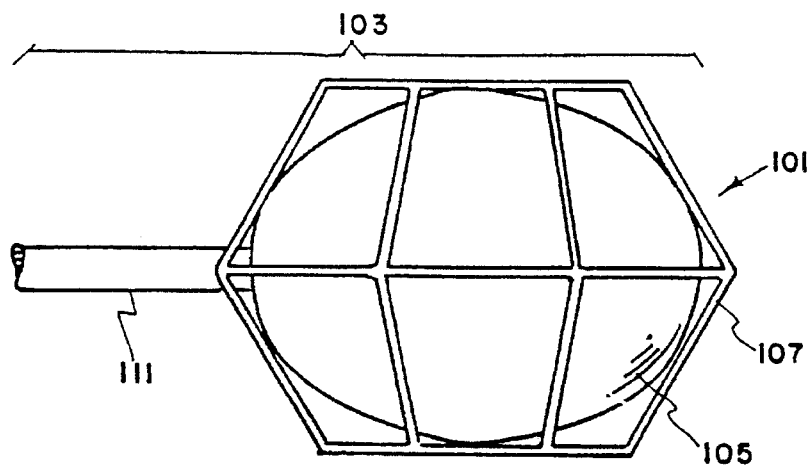
FIG. 8A is a schematic representation of a Type IV inflatable retraction device according to a second aspect of the invention.

FIG. 8A is a schematic representation of a basic Type IV inflatable retraction device according to the second aspect of the invention. The Type IV inflatable retraction device is shown in its expanded condition. The Type IV inflatable retraction device 101 has two main components, the inflatable retractor 103 and the maintainer 107. Both the inflatable retractor and the maintainer are in a collapsed condition when the Type IV inflatable retraction device is inserted into the body.

The first main component of the Type IV inflatable retraction device, the inflatable retractor 103, has a main inflatable chamber 105 that is inflated to retract an organ into a retracted condition. The second main component, the maintainer 107 is expanded, at least partially by inflating the inflatable retractor, to maintain the retracted organ in its retracted condition and to allow the inflatable retractor 103 to be deflated and possibly, removed.

The structure of the inflatable retractor 103 does not permit instruments to pass through it to treat the tissue. The maintainer 107 has an open structure that enables instruments to pass through it to treat the tissue once the inflatable retractor 103 has been deflated and, possibly, removed. The maintainer 107 may have several different constructions that will be described below.

(a) Type IVA Inflatable Retraction Device

Figure 8B:
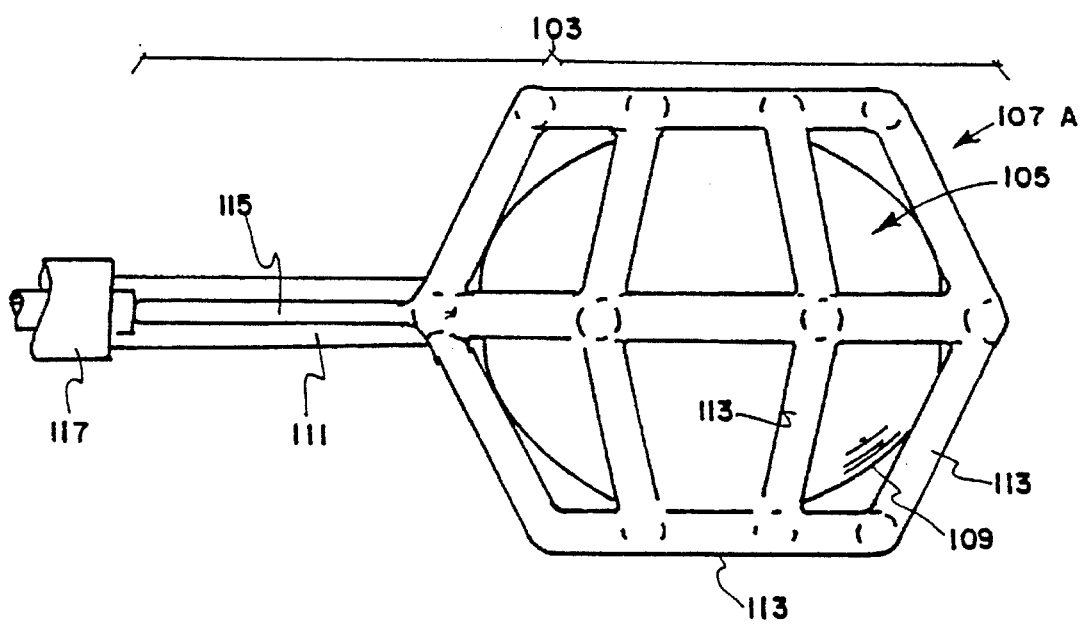
FIG. 8B is a perspective view of a Type IVA inflatable retraction device according to a second aspect of the invention having an external inflatable maintainer.

FIG. 8B shows a Type IVA inflatable retraction device which has an inflatable maintainer 107A. The main inflatable chamber 105 of the inflatable retractor 103 is enclosed by a main envelope 109, which is preferably a balloon of a suitable elastomeric material such as latex, polyurethane, or silicone rubber. The size and shape of the main inflatable chamber 105 depends on the application. For a given inflated size, a main envelope made of an elastomeric material has considerably less collapsed bulk than a main envelope made of a non-elastic material, such as Mylar®, polyethylene, polyethylene/nylon composite, etc. Moreover, the main envelope of a Type IVA inflatable retraction device can be considerably lighter and thinner than the main envelope of a Type I retraction device because it need only remain inflated for a few minutes, and is subject to considerably lower pressures. The main inflatable chamber is inflated by an inflation gas passed through the main inflation tube 111.

The inflatable maintainer 107A shown in FIG. 8B is a geodesic structure formed from a plurality of interconnected inflatable plastic tubes 113. The tubes 113 are formed from a substantially inelastic plastic material such as Mylar® or polyethylene, or, preferably, a polyethylene/nylon composite. The tubes are interconnected so that their bores communicate, which enables the maintainer to be inflated by the single additional inflation tube 115. The size and shape of the tubes 113 depends on the application. For instance, a Type IV inflatable retractor suitable for retracting the bowel and lifting the liver to gain access to the gall bladder has a structure in which the tubes 113 are on the edges of a dodecahedron in the range 8" to 12" (20 to 30 cm across. Each tube is 0.4" to 0.8" (10 to 20 mm) in diameter, and has a wall thickness in the range 4 to 10 mil. (0.1 to 0.25 mm).

(b) Type IVA Inflatable Retraction Device—Method of Use

For insertion into the body, the Type IVA inflatable retraction device is packaged as follows. The main inflatable chamber 105 of the inflatable retractor 103 is preferably lightly attached to the maintainer 107A before the inflatable retraction device 103 is packaged in its collapsed state. This is to ensure that the main inflatable chamber remains inside the maintainer when the main inflatable chamber is inflated. The main inflatable chamber and the maintainer are inflated with the main inflatable chamber inside the maintainer, and are attached to one another using a suitable adhesive, or by welding.

Figure 9A:
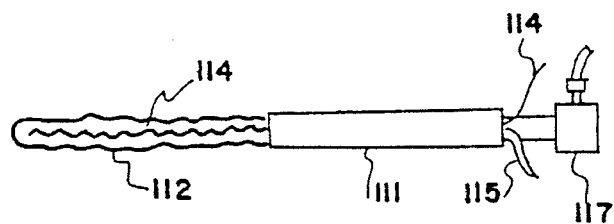
FIG. 9A shows a Type IVA inflatable retraction device with an inflatable maintainer according to the invention in its packaged state prior to insertion into the body.

The main inflatable chamber 105 and the maintainer 107A are then both evacuated to collapse them, and then are packaged to form an extension of the main inflation tube 111 and the additional inflation tube 115. The collapsed inflatable retraction device is held in its packaged condition by the sleeve 112 with detachable lacing 114, as shown in FIG. 9A. Alternatively, the collapsed retraction device can be held in its collapsed condition by detachable lacing, by a sleeve with a tear strip, or by another suitable method. The packaged assembly has an overall diameter of about 11 mm, which enables the package to fit through a 12 mm trocar tube.

Figure 9B:
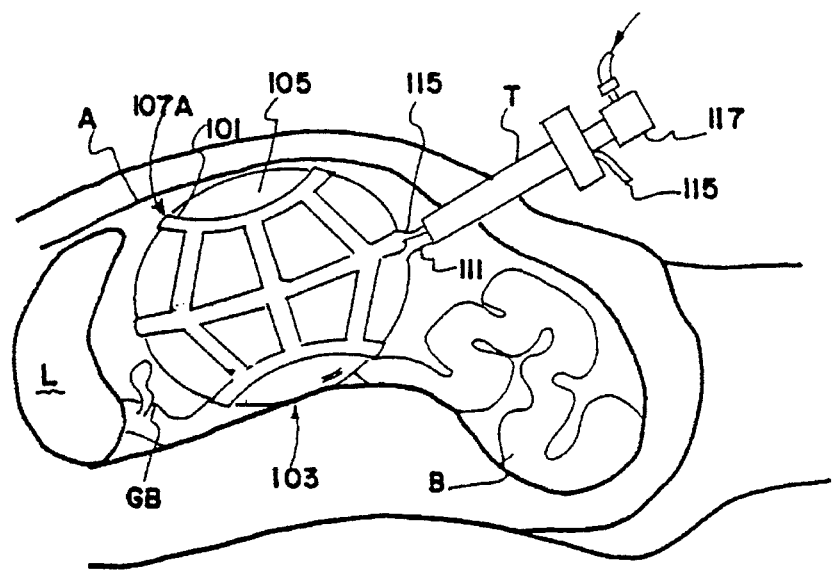
FIGS. 9B through 9E show cross sectional views of the abdomen including the bowel, the liver, and the gall bladder to illustrate the method according to the invention of using a Type IVA inflatable retraction device with an inflatable maintainer according to the invention to retract the bowel and lift the liver to gain access to treat the gall bladder.

FIGS. 9B through 9E illustrate the method according to the invention of using the Type IVA inflatable retraction device 101 in the abdomen A to retract the bowel B and to lift the liver L to gain access to treat the gall bladder GB. The method can also be used to treat other organs and tissues in the body. The packaged inflatable retraction device 101 is inserted into the body through a suitable trocar tube T and placed adjacent to the tissue to be treated, i.e., the gall bladder GB. The inflatable retraction device 101 is released from the sleeve 112 by pulling on the detachable lacing 114 (FIG. 9A). The main inflation tube 111 is connected to a source of inflation gas (not shown) and the inflation gas pressure is increased until the main inflatable chamber 105 begins to expand. When the main inflatable chamber expands, it gently retracts the bowel B and lifts the liver L, and also extends maintainer 107A over its surface, as shown in FIG. 9B.

Figure 9C:
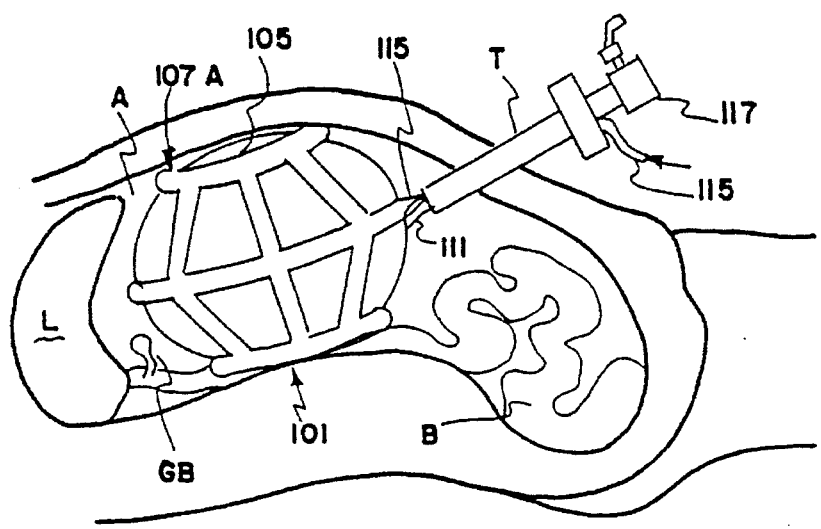

When the main inflatable chamber 105 is expanded to the limits defined by the maintainer 107A, inflation is stopped, the first inflation tube 111 is clamped, and the source of inflation gas is transferred to the additional inflation tube 115. The maintainer is then inflated to a fully expanded condition, as shown in FIG. 9C. This requires a pressure in the range 5 to 10 pounds per square inch (3.5 to 7 kPa).

Inflation of the maintainer 107A may be begun before the main inflatable chamber 105 is fully inflated, if desired. An endoscope can be introduced into the main inflatable chamber through a gas-tight port 117 on the main inflation tube 111 to check the position of the maintainer. If the maintainer obstructs access to the tissue to be treated, the partially inflated maintainer can be manipulated to change its position. The maintainer and the main inflatable chamber are then fully inflated.

Once the maintainer 107A is fully inflated, the inflation pressure to the main inflatable chamber 105 is gradually released. During deflation of the main inflatable chamber, the structural integrity of the maintainer is observed to ensure that the maintainer retains the retracted organ in its retracted condition. Manipulation of the maintainer may be necessary to ensure that the organ remains adequately retracted.

Figure 9D:
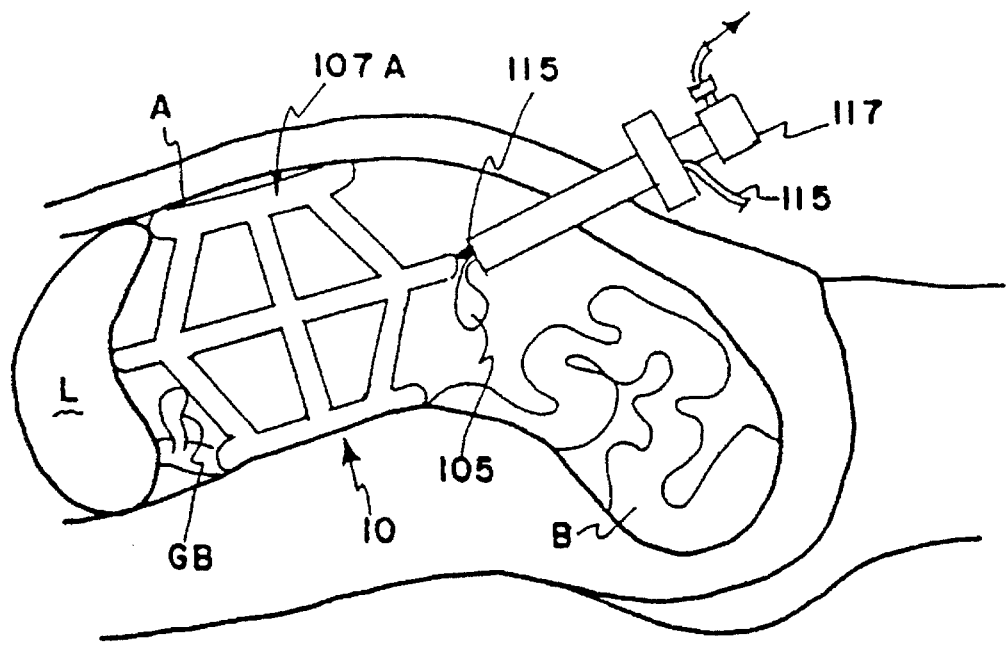
Figure 9E:
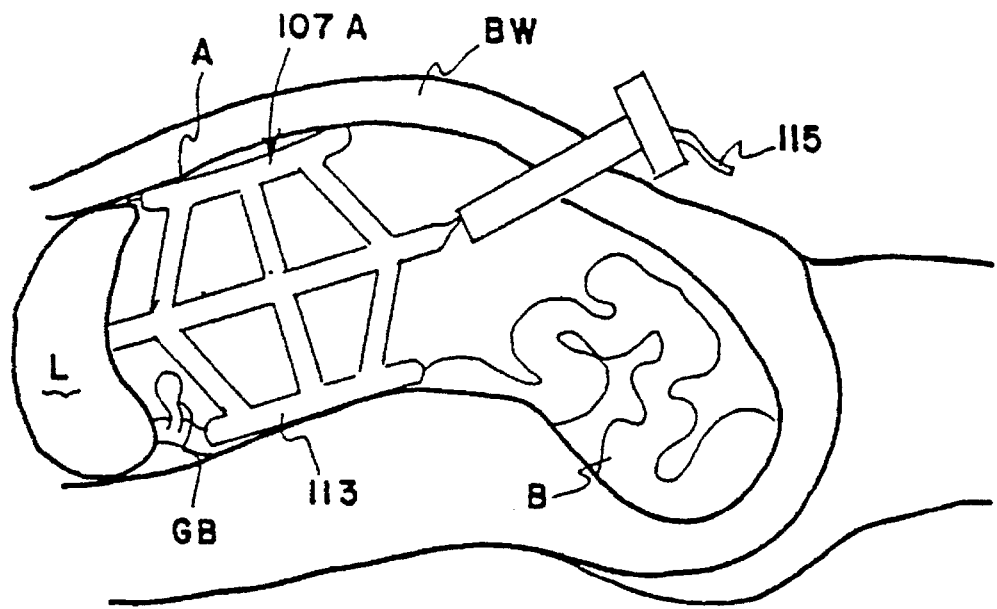

Deflating the main inflatable chamber 105 detaches it from the maintainer 107A. Once the main inflatable chamber is fully deflated, as shown in FIG. 9D, it is evacuated to collapse it, and the inflatable retractor is removed from inside the maintainer, and removed from the body, leaving the maintainer alone to keep the bowel retracted and the liver lifted, as shown in FIG. 9E.

The tissue is then treated using instruments passed into the body through suitable incisions in the body wall BW. The instruments are passed through the large windows between the inflatable tubes 113 of the maintainer. The maintainer has no external envelope, so no time need be spent cutting apertures to gain access to the tissue to be treated.

(c) Type IVA Inflatable Retraction Device with Internal Inflatable Maintainer

Figure 8C:
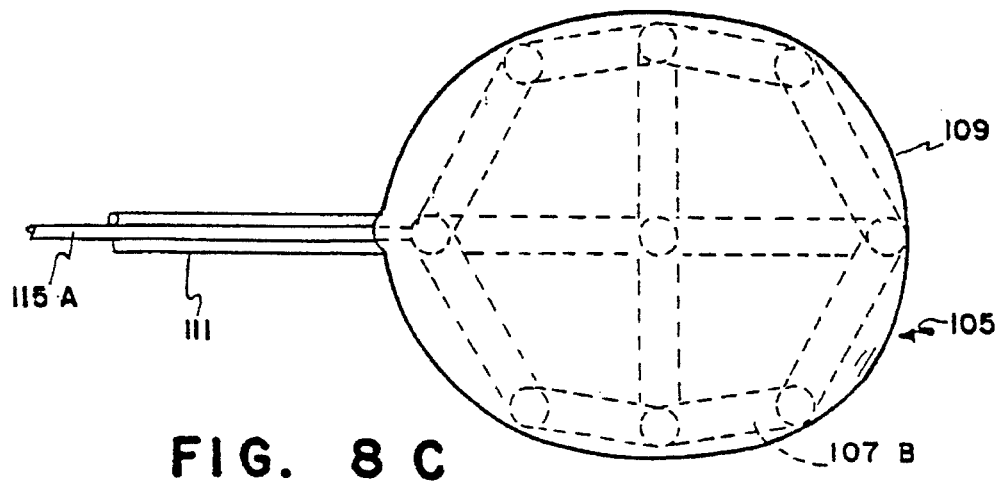
FIG. 8C is a cut-away perspective view of a Type IVA inflatable retraction device according to a second aspect of the invention having an internal inflatable maintainer.

The Type IVA inflatable retraction device may also be packaged with an inflatable maintainer 107B inside the main inflatable chamber 105. An internal maintainer eliminates the risk of the main inflatable chamber 105 escaping from inside the maintainer 107B during inflation of the main inflatable chamber. Although the maintainer cannot escape from the main inflatable chamber, it is still desirable to attach the maintainer to the inside of the main envelope 109. Inflating the main inflatable chamber partially expands the maintainer 107B before it is inflated, which makes it easier to inflate the maintainer. The inflatable retraction device, with the main inflatable chamber in its inflated condition, is shown in FIG. 8C.

The internal maintainer variation of the Type IVA inflatable retraction device is deployed by the same method as the external maintainer variation described above. However, after inflation pressure has been removed from the main inflatable chamber 105, the main envelope 109 cannot simply be withdrawn from the outside of the maintainer. Instead, it must be cut up and removed. Alternatively and preferably, it is left in place during treatment, and apertures are cut in the main envelope through which treatment can be carried out. Leaving the main envelope in place enables the tissue to be pulled through the aperture in the main envelope and treated inside the main envelope. The aperture in the main envelope forms a seal around the tissue being treated, and blood, debris, etc. are retained inside the main envelope, whence they can easily be removed.

(d) Type IVA Inflatable Retraction Device with Mechanical Maintainer

The inflatable maintainer 107A of a Type IVA inflatable retraction device can be replaced by a mechanical maintainer having a bistable folding rib structure of metal, plastic, or some other suitable material. Inflating the main inflatable chamber retracts the organ, and also partially unfolds the ribs of the maintainer into an expanded condition as the main inflatable chamber expands. Inflating the main inflatable chamber further fully expands the maintainer by driving its ribs into a stable, over-center condition. When the inflation pressure in the main inflatable chamber is reduced, the ribs stay in their over-center condition. In this condition, the maintainer has structural integrity and can maintain the organ retracted by the main inflatable chamber in its retracted condition.

The mechanical maintainer of a Type IVA inflatable retraction device is removed at the end of the treatment by dismantling it or cutting it up. Alternatively, an inflatable retractor can once more be placed inside the maintainer and inflated to return the ribs from their over-center condition. The inflatable retractor is then deflated, which enables the maintainer to collapse into its folded condition. The maintainer is then removed in its folded condition along with the inflatable retractor.

(e) Type IVB Inflatable Retraction Device

Figure 10A:
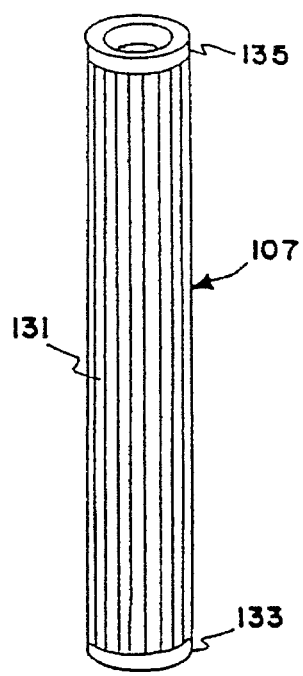
FIGS. 10A through 10D illustrate a Type IVB inflatable retraction device according to a second aspect of the invention having a mechanical maintainer.

The Type IVB inflatable retraction device uses the simple mechanical maintainer shown in FIG. 10A. The maintainer 107C comprises a first hub 133 and a second hub 135 interconnected by a plurality of strips or wires 131 of a malleable metal or plastic. Aluminum or steel is preferred. Alternatively, the maintainer can be made by making a number of longitudinal cuts almost from end-to-end of a tube of a suitable malleable material. The outside diameter of the maintainer 107C is about 11 mm, which enables it to pass easily through a 12 mm introducer sleeve.

Figure 10B:
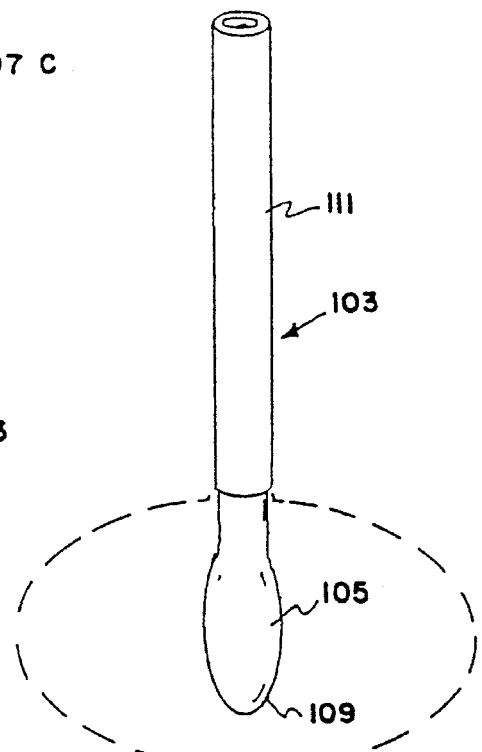

In FIG. 10B, the main inflatable chamber 105 of the inflatable retractor 103 is preferably a balloon enclosed by a main envelope 109 of a suitable elastomeric material such as latex or silicone rubber. The size and shape of the main inflatable chamber 105 depends on the application. Using an elastomeric material for the main envelope enables an envelope of the required strength and inflated size to fit within the maintainer 107C. The main inflatable chamber is inflated by an inflation gas passed through the main inflation tube 111.

Figure 10C:
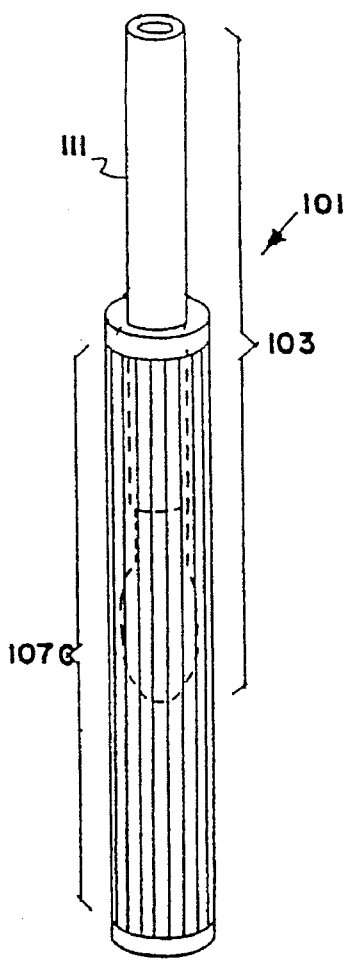

Before insertion into the body, the retractor 103 is assembled with the maintainer 107C, as shown in FIG. 10C. The main inflation tube 111 is temporarily attached to the maintainer to make a single unit for insertion.

Figure 10D:
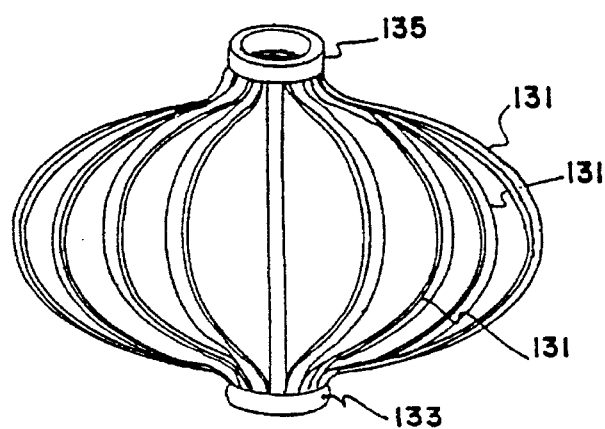

After the inflatable retraction device 101 is inserted into the body, the main inflatable chamber 105 is inflated by passing an inflation fluid through the inflation tube 111. The main inflatable chamber expands radially, which retracts the organ, and displaces the strips 131 of the maintainer radially outwards. This reduces the overall length of the maintainer. FIG. 10D shows the shape of the maintainer in its expanded condition at the end of the inflation process.

After the main inflatable chamber 105 is fully inflated, and the maintainer is in its expanded condition, as shown in FIG. 10D, the inflation pressure in the main inflatable chamber is released, and the main inflatable chamber returns to its collapsed condition. The maintainer 107C in its expanded condition is sufficiently strong to maintain the organ in its retracted condition. The main inflation tube 111 is then detached from the maintainer, and the retractor 103 is withdrawn from the body. The tissue is treated by instruments passing from outside the body through the spaces between the strips 131 of the maintainer 107C.

Alternatively, the main inflatable chamber 105 can be released from the end of the main inflation tube 111 and removed from the body. The main inflation tube is then used as a duct through which to pass instruments from outside the body to treat the tissue. The instruments pass from outside the body into the interior of the maintainer, and then pass through the spaces between the strips 131 of the maintainer 107C to treat the tissue.

3. HIGH-STRENGTH INFLATING METHOD

A method according to the third aspect of the invention for inflating Type I, Type III, and Type IV inflatable retraction devices having a second or additional inflatable chamber (an "additional inflatable chamber") enables the collapsed bulk of such inflatable retraction devices to be reduced. The additional inflatable chamber of any of the above-mentioned inflatable retraction devices relies on the rigidity of its envelope under inflation pressure for its strength. To provide the strength required, the additional inflatable chamber must have a relatively large cross sectional area and use a relatively high inflation pressure (about ten times that used in the main inflatable chamber). This in turn requires that the envelope of the additional inflatable chamber be relatively thick. The large area of relatively thick material required for the envelope of the additional inflatable chamber contributes significantly to the collapsed bulk of the inflatable retraction device.

The method according to the invention of filling the additional inflatable chamber of an inflatable retraction device fills the additional inflatable chamber with a fluid that, once in place, is made rigid. This enables the whole cross sectional area of the additional inflatable chamber to contribute to the strength of the additional inflatable chamber. For a given strength, the cross-sectional area of the additional inflatable chamber can be reduced, and lower pressures can be used, which enables a smaller area of a thinner material to be used for the envelope of the additional inflatable chamber. This results in a useful reduction in the collapsed bulk of the additional inflatable chamber, and hence in the collapsed bulk of the inflatable retraction device as a whole.

In inflatable retraction devices in which the envelope of the main inflatable chamber forms part of the envelope of the additional inflatable chamber, a thinner material may also be used for the envelope of the main inflatable chamber, giving a further reduction in the collapsed bulk of the inflatable retraction device.

In the method according to the invention, the main chamber of the inflatable retraction device is inflated in the normal way. The additional inflatable chamber is theft filled with a slurry of a non-soluble particulate solid in a fluid. Preferably, the slurry is a slurry of glass beads in water. Beads in the range 0.040" to 0.080" (1 to 2 mm) in diameter are preferred. Alternatively, the beads can be of a suitable plastic, such as polycarbonate or acrylic. The additional inflatable chamber is preferably filled by evacuating it, and then pumping the slurry in to fill it.

The fluid is removed from the additional inflatable chamber, leaving the particulate solid behind. This is preferably done by inserting into the inflation tube a filter with a mesh small enough to trap the particulate solid while allowing the fluid to pass. The fluid is then pumped out through the filter. The particulate solid is then compacted by evacuating the additional inflatable chamber. With the additional chamber evacuated, ambient air pressure acting against the envelope of the additional inflatable chamber pushes the particulate solid together, and expels fluid from between the particles of the solid. This greatly increases the friction between the particles and allows the particles to bind together to form a pseudo-solid structure.

Treatment is carried out working through the inflatable retraction device as normal. When treatment is complete, the vacuum is released, and fluid is pumped back into the additional chamber once more to wash the particulate solid out of the additional inflatable chamber and to allow the inflatable retraction device to be removed from the body.

Figure 11C:
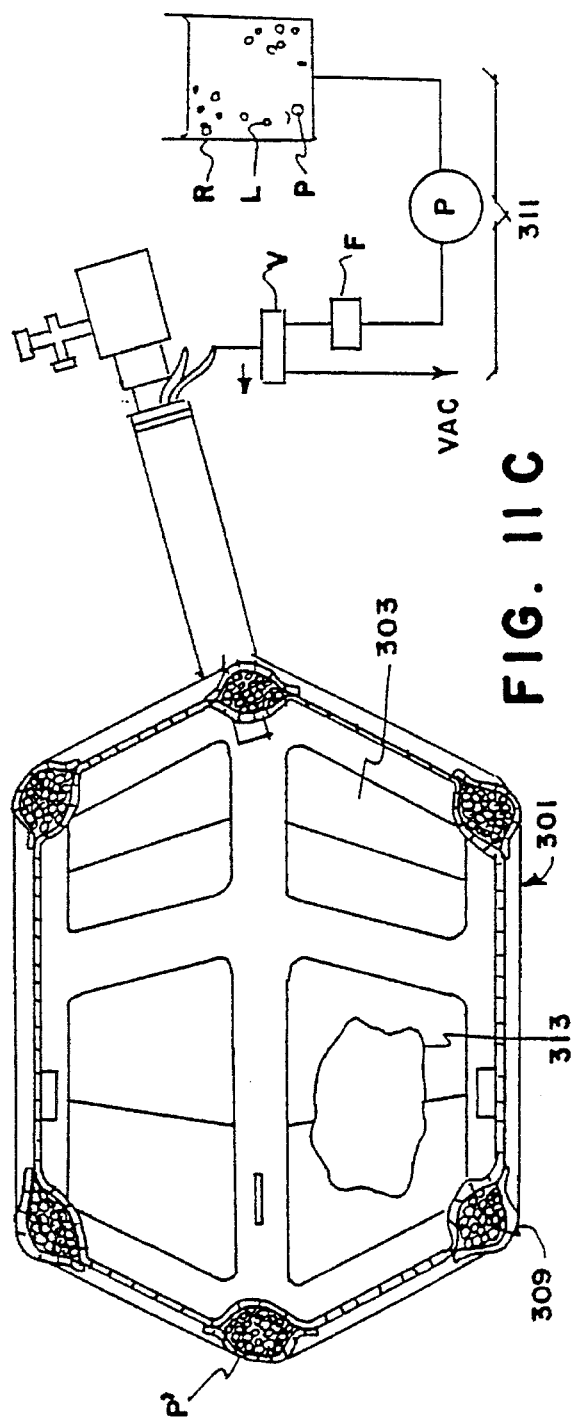

The method according to the invention is illustrated in FIGS. 11A through 11C, which show a polyhedral Type IA inflatable retraction device 301. The main inflatable chamber 303 is inflated with a suitable inflation gas passed through the main inflation tube 305 in the normal way. The additional inflation tube 307 for filling the additional inflatable chamber 309 is connected to the slurry filling apparatus 311.

The slurry filling apparatus comprises a reservoir R for the slurry S. The slurry S comprises particles, such as the particle P, of a particulate solid in a liquid L. The reservoir R has a slurry outlet that is connected to the forward inlet of the reversible pump P. The forward outlet of the reversible pump P is connected through the switchable filter F to the first port of the 2-way valve V. The second port of the 2-way valve V is connected to a vacuum line VAC. The common port of the 2-way valve V is connected to the second inflation tube 307.

The 2-way valve V is set to connect its first port to the common port and the filter F is set to its off position. The pump P is operated in its forward direction to pump the slurry S into the additional inflatable chamber 309. The inflatable retraction device 301 with its main inflatable chamber 303 inflated with inflation gas and its additional inflatable chamber filled with slurry S is shown in FIG. 11A. The slurry S in the additional inflatable chamber comprises particles, such as the particle P', of a particulate solid in the liquid L.

The filter F is then switched to its on position and the pump P is reversed. The pump P pumps the slurry S out of the additional inflatable chamber 309, but the filter F traps the particles of the particulate solid component of the slurry remain inside the additional inflatable chamber, and only the liquid component L of the slurry S is returned to the reservoir R. The inflatable retraction device 301 with its main inflatable chamber 303 inflated with inflation gas and its additional inflatable chamber filled with particles, such as the particle P', of the particulate solid component of the slurry is shown in FIG. 11B.

The 2-way valve V is then set to connect its second port to its common port. This connects the vacuum line VAC to the additional inflation tube 307. The vacuum line VAC reduces the pressure inside the additional chamber 309. External pressure on the envelope of the additional chamber forces the envelope inwards and consolidates the particles of the particulate solid. Inflation pressure in the main inflatable chamber 303 is then released. FIG. 11C shows the inflatable retraction device 301 after the additional inflatable chamber 309 has been evacuated. The particles, such as the particle P', of the particulate solid component of the slurry are compacted and provide the additional inflatable chamber 309 with considerably more strength than if the additional inflatable chamber were filled with an inflation gas. The main inflatable chamber 303 is in its depressurized state and an aperture 313 has been cut in the envelope of the main inflatable chamber to provide access to the organ to be treated.

The 2-way valve V and the vacuum line VAC can be dispensed with if the pump P is capable of pulling a vacuum of more than x mm of mercury (kPa). The pump P is the left running after all the liquid has been removed from the additional inflatable chamber 309 to reduce the pressure in the additional inflatable chamber and consolidate the particulate solid.

With relatively small retraction devices, a large syringe can be used for the pump P and the reservoir R. The same or a different syringe can also be used to evacuate the additional inflatable chamber.

Figure 11D:
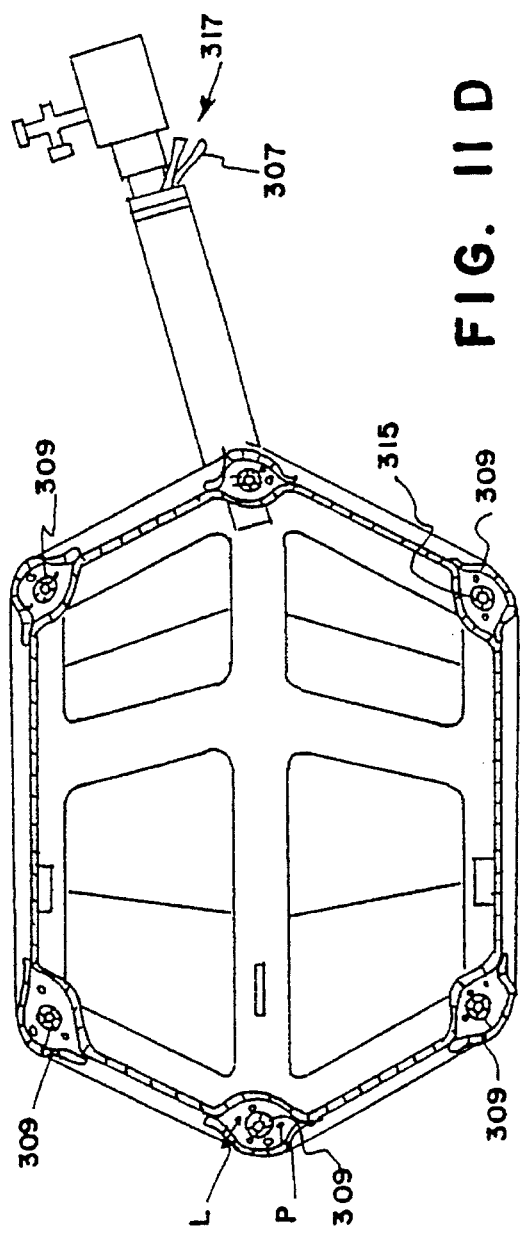

Particulate solids other than glass beads can be compacted by heating them or cooling them. Moreover, with such particulate solids, it may not be necessary to remove the liquid component of the slurry before compacting takes place. FIG. 11D shows the Type IA inflatable retraction device 321, which includes the inner pipe 309 running through the additional inflatable chamber 309. Once the additional inflatable chamber has been filled with the slurry, and the liquid component of the slurry removed, if necessary, a fluid at a suitable temperature is circulated through the inner pipe inlet 317, an inner pipe outlet (not shown), and the inner pipe 315. The temperature change caused by the fluid circulating in the inner pipe 315 consolidates the matter filling the additional inflatable chamber. If the particulate solid is consolidated by heating, a suitable electrical heating element can be substituted for the inner pipe 315.

4. SELF-RETRACTING ENDOSCOPE

During endoscopic observation within the body, it is often impossible to see a wide enough area at one time because other organs or tissues obstruct the field of view of the endoscope. Retraction devices of the type described in this application, in the prior application, and elsewhere can be used to provide retraction and obtain an unobstructed view. The process of correctly positioning the retraction device, deploying it, opening up one or more observation windows, and removing the retraction device after the observations are complete is cumbersome. A self-retracting endoscope according to the fourth aspect of the invention provides local retraction in the vicinity of the distal end of the endoscope to provide an unobstructed wide field of view.

(a) Inflatable Self-Retracting Endoscope

An inflatable self-retraction endoscope 201 according to the invention is shown in FIGS. 12A through 12D. The self retracting endoscope 201 comprises a substantially tubular optical assembly 203 and an inflatable retraction device 205. The optical assembly 203 can be the same as the optical assembly used in known optical or video endoscopes.

The inflatable retraction device 205 is attached to the outer surface 207 of the optical assembly 203, close to the distal end of the optical assembly. The inflatable retraction device 205 is provided with an inflation tube 209 through which it is inflated into the expanded condition shown in FIG. 12A, once inside the body.

The inflatable retraction device, when inflated, is shaped like a hollow frustum of a cone having its narrow end towards the optical assembly 203. The shape of the inflatable retraction device 205 is designed such that it does not obstruct the peripheral view from the optical assembly 203 when the optical assembly is set to its widest viewing angle.

In the preferred embodiment, the inflatable retraction device 205 comprises a stack of toroidal balloons 211 made of a suitable elastomeric or non-elastomeric flexible material. The diameter of the toroidal balloons increases in the distal direction to prevent the inflatable retraction device from reducing the field of view of the optical assembly 203.

Figure 12:
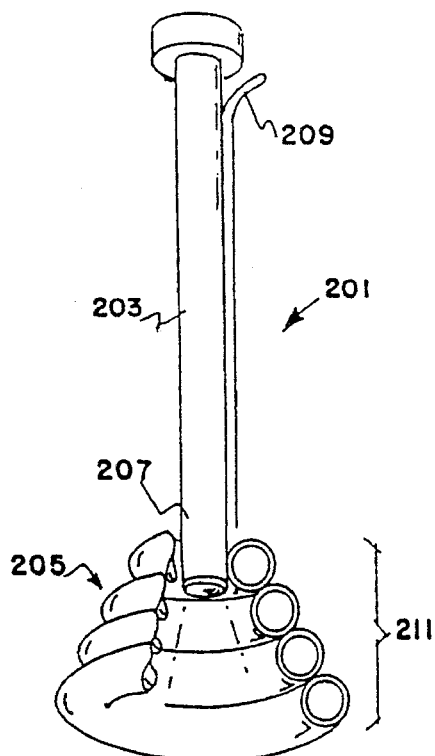
FIGS. 12A through 12G illustrate a self-retracting endoscope according to a fourth aspect of the invention.
Figure 12:
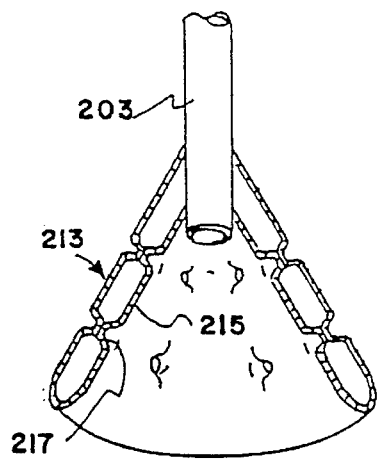
Figure 12:
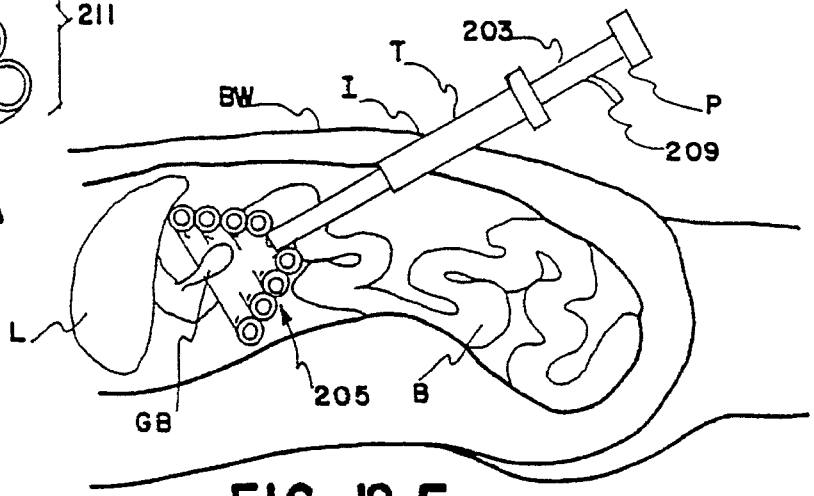
Figure 12:
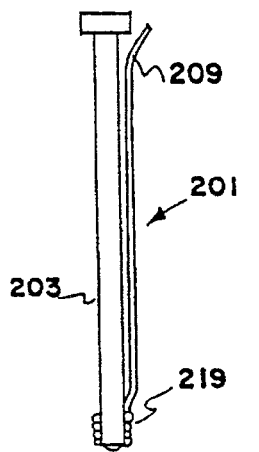
Figure 12:
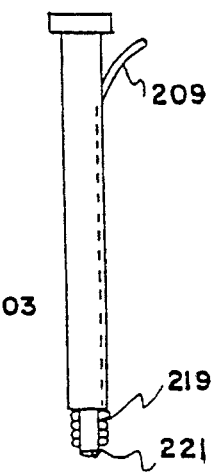
Figure 12:
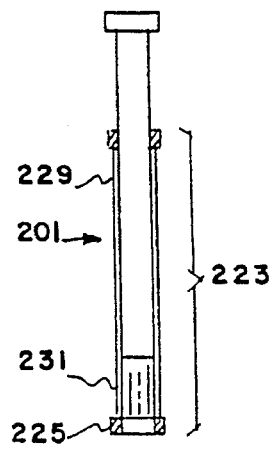
Figure 12:
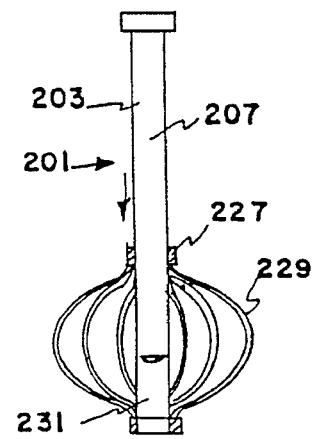

Alternatively, the version of the inflatable retraction device 205 shown in FIG. 12B can be made from two sector-shaped pieces of an inelastic flexible material 213 and 215, respectively. Opposing straight sides of each piece of material are connected together to form a truncated cone. The truncated cone formed from material 213 is placed over the truncated cone made from the material 215, and the curved sides of the truncated cones are joined together. The slanting sides of the truncated cones are also tacked together with the tacks 217 to give the resulting hollow frustum substantially parallel inner and outer slanting sides.

The self-retracting endoscope 201 is supplied with the inflatable retraction device packed in a collapsed condition 219 flat against the outer surface 207 of the optical assembly 203, as shown in FIG. 12C. An alternative construction of the self-retracting endoscope 201 for use in an insufflated body cavity is shown in FIG. 12D. The optical assembly 203 includes a waisted portion 221 that accommodates the inflatable retraction device in its collapsed state 219 within the overall diameter of the optical assembly. The optical assembly 203 also accommodates the inflation tube 209 internally so that the self-retracting endoscope 201 has a substantially constant circular cross-section that can form a seal with the gas-tight port of a trocar tube.

(b) Method of Using the Self-Retracting Endoscope

The method according to the invention of using the self-retracting endoscope 201 according to the invention to make observations within a body cavity is illustrated in FIG. 12E, in which the endoscope is used to observe the gall bladder. An incision I is made in the abdominal wall BW. A trocar tube T is inserted and the abdomen is insufflated using known techniques to provide working space. The self-retracting endoscope 201 is inserted into the abdomen through the gas-tight port P on the trocar tube T and is advanced past the bowel B and under the liver L into the vicinity of the gall bladder GB.

With a conventional endoscope, part of the gall bladder can be observed, but attempts to see the gall bladder as a whole are thwarted by the liver L. When the conventional endoscope is drawn away from the gall bladder GB to obtain a view of the gall bladder as a whole, the liver drops back into place and obstructs the view.

In the method according to the invention of using the self-retracting endoscope 201 according to the invention, the distal tip of the endoscope is placed close to the surface of the gall bladder GB, and a source of inflation gas (not shown) is attached to the inflation tube 209. The inflation gas pressure is gradually increased to expand the inflatable retraction device 205. As the inflatable retraction device 205 expands, it pushes the distal tip of the endoscope away from the gall bladder, enlarging the field of view, and retracting the liver to prevent the liver from obstructing the view of the gall bladder.

After the observations have been made, the inflation pressure in the inflatable retraction device 205 is released to collapse the inflatable retraction device. The inflatable retraction device is then evacuated to retract it fully. The distal tip of the self-retracting endoscope 201 can then be moved to a different observation site (if accessible from the incision I) and the inflation-observation-deflation sequence is repeated. In some circumstances, it may not be necessary to deflate the inflatable retraction device to change the observation site.

(c) Self-Retracting Endoscope with Mechanical Retractor

A self-retracting endoscope with a mechanical retractor according to the fourth aspect of the invention is shown in FIGS. 12F and 12G. The self-retracting endoscope 201 comprises a substantially tubular optical assembly 203 and an expandable mechanical retractor 223. The optical assembly 203 can be the same as the optical assembly used in known optical or video endoscopes.

The expandable mechanical retractor 223 comprises a fixed hub 225 and a slidable hub 227. The fixed hub 225 and the slidable hub 227 are interconnected by a plurality of springy metal or plastic strips or wires 229. In the preferred embodiment, optical quality transparent strips are used. The fixed hub 225 is affixed to the extension 231 on the distal end of the optical assembly 203. The extension 231 can be a plurality of thin, stiff wires, or can be a hollow cylinder of a transparent plastic. The expandable mechanical retractor is expanded by sliding the slidable hub 227 axially along the outer surface 207 of the optical assembly by a suitable mechanism (not shown). The mechanism allows the slidable hub to be locked in position to keep it in its expanded condition. In its expanded condition, the expandable mechanical retractor retracts organs obstructing the field of view from the distal end of the optical assembly.

FIG. 12F shows the expandable mechanical retractor in its collapsed condition with the strips 229 of the retractor lying substantially parallel to the outer surface 207 of the optical assembly. The self-retracting endoscope is inserted into the body in this state. FIG. 12G shows the expandable mechanical retractor 223 in its expanded condition. The slidable hub 227 has been slid in the distal direction axially along the outer surface 207 of the optical assembly 203 and has been locked in place. This causes the strips 229 to move radially outwards to form the structure shown in FIG. 12G, which retracts organs or tissues that would otherwise obstruct the view from the optical assembly. Observations are carried out looking though the strips 229 and the extension 231. After observations have been completed, the slidable hub 227 is slid proximally along the outer surface 207 of the optical assembly to return the expandable retractor to its collapsed condition so that the self-retracting endoscope can be withdrawn from the body cavity.

5. INSERTION TUBE

Inflatable retraction devices in their collapsed state have conventionally been packed in a substantially cylindrical package for insertion into the body prior to deployment. The cylindrical package has conventionally been introduced into the body by pushing it through a suitably-sized trocar tube or introducer sleeve. If the outside diameter of the package has been close to the diameter of the diameter of the bore of the trocar tube, there is a tendency for the package to stick in the bore of the trocar tube. Pushing the package harder causes the package to buckle, and wedges the package more firmly. An insertion tube according to a fifth aspect of the invention draws the packaged retraction device into the body and avoids problems with the package sticking.

(a) Insertion tubes

The most basic form of the insertion tube 241 according to the fifth aspect of the invention is shown in FIG. 13A. The insertion tube 241 comprises a tube 243 and a string 249 having a first end 251 and a second end 253. The first end 251 of the string passes distally outside the tube 243. At the distal end 244 of the tube, the first end of the string passes into the bore 247 of the tube, passes proximally through the bore, and emerges from the proximal end 246 of the tube. The first end 251 of the string is attached to the proximal end 255 of the packaged inflatable retraction device 257. To reduce friction between the string 249 and the distal end 244 of the tube, the tube 243 should have a relatively thick wall, and the distal end 244 should be rounded. A radial groove can be made in the distal end to locate the string, if desired.

A less basic form of the insertion tube 241 according to the fifth aspect of the invention is shown in FIG. 13B. The insertion tube 241 comprises a tube 243 having a small eyelet 245 attached to its distal end 244. The insertion tube 241 also comprises a string 249 having a first end 251 and a second end 253. The first end 251 of the string passes distally through the bore 247 of the tube, through the eyelet 245, passes proximally back through the bore, and emerges from the proximal end 246 of the tube. The first end 251 of the string is attached to the proximal end 255 of the packaged inflatable retraction device 257.

An improved variation of the insertion tube 241 according to the invention is shown in FIG. 13C. In the improved variation, the string is contained within the insertion tube, unlike the version shown in FIG. 13A, and the bore 247 of the tube 243 lacks the eyelet 245 that could snag the packaged inflatable retraction device 257 in the version shown in FIG. 13B. The improved version of the insertion tube 241 has a narrow-bore tube 255 attached to the outer wall 257 of the tube 243. The distal end of the narrow-bore tube extends slightly beyond the distal end of the tube 243 to aid in ejecting the packaged inflatable retraction device 257 from the bore 247. To give the insertion tube a smooth outer wall, the tube 243 and the narrow-bore tube 255 are enclosed in an outer tube 259.

The narrow-bore tube 255 can also be attached to the bore 247 of the tube, as shown in FIG. 13D. This eliminates the need for the outer tube 249.

In the versions of the insertion tube shown in FIGS. 13C and 13D, the first end 251 of the string 249 passes distally through the bore of the narrow-bore tube 255. At the distal end of the narrow-bore tube, the first end of the string enters the bore 247 of the tube 243, passes proximally through the bore 247, and emerges from the proximal end 246 of the tube. The first end 251 of the string is attached to the proximal end 255 of the packaged inflatable retraction device.

(b) Method of Using an Insertion Tube

The method according to the invention of placing a substantially cylindrical package, for example, an packaged inflatable retraction device, into the body using an insertion tube according to the invention is as follows. The distal end of the insertion tube is inserted into the body by inserting it into a trocar tube in place in the body. If the body is insufflated, the insertion tube is passed through a gas-tight port on the trocar tube, and is fitted with a gas-tight port itself. The insertion tube is manipulated to bring its distal end close to the point at which it is desired to deposit the inflatable retraction device. The first end 251 of the string is attached to the proximal end 255 of the packaged inflatable retraction device. The distal end of the packaged inflatable retraction device is inserted into the proximal end of the bore 247 of the tube, and the packaged inflatable retraction device is pushed into the bore of the tube as far as it will go.

The insertion tube 241 is then grasped with one hand and the second end 253 of the string is grasped with the other. The second end of the string is then pulled proximally to draw the packaged inflatable retraction device through the bore 247 of the tube. Because the first end 251 of the string is attached to the proximal end 255 of the packaged retraction device, a final pull on the second end 253 of the string ejects the packaged inflatable retraction device from the bore of the tube. The insertion tube 241 is then withdrawn from the trocar tube, and the inflatable retraction device is released from its packaging. This also detaches the string; 249 from the inflatable retraction device. The string 249 and the packaging are withdrawn from the body through the trocar tube. The inflatable retraction device is then deployed in the normal way.

We claim:

1. Apparatus for retracting an organ inside the body to gain access to an adjacent tissue, the apparatus comprising:

a main inflatable chamber having an envelope of an elastomeric material;

maintaining means operatively associated with the inflatable chamber and having a substantially cylindrical shape in a collapsed state without application of external force; and means for selectively inflating the main inflatable chamber while in place within the body to retract the organ into a retracted condition and to expand the maintaining means to an expanded state, the maintaining means in the expanded state having a substantially spheroidal shape and an open structure; and wherein the maintaining means is structured to retain the expanded state after the main inflatable chamber is deflated to maintain the organ in the retracted condition and to provide access to the tissue after the main inflatable chamber is deflated.

2. The apparatus of claim 1, wherein:

the maintaining means comprises plural strips of a malleable material arranged to form a curved surface of a cylinder, and the main inflatable chamber is inside a space bounded by the curved surface of the maintaining means.

3. The apparatus of claim 1, wherein the maintaining means comprises:

a first hub and a second hub, each hub being cylindrical and having a curved outer surface; and plural strips of a malleable material, each strip having a first end and a second end, the first end being attached to the curved outer surface of the first hub, and the second end being attached to the curved outer surface of the second hub.

4. The apparatus of claim 1, wherein the maintaining means comprises a hollow cylinder of a malleable material, the hollow cylinder having a curved sidewall, a first end, and a second end, the curved sidewall being pierced by plural longitudinal cuts each extending from a point adjacent to the first end to a point adjacent to the second end to form plural strips interconnecting the first end and the second end.

5. A method of retracting an organ inside the body to gain access to an adjacent tissue, the method comprising steps of:

(a) providing a main inflatable chamber and a maintainer in a collapsed state, the maintainer having a substantially cylindrical shape in the collapsed state without application of external force, the maintainer being structured to retain an expanded state following expansion to the expanded state, the maintainer in the expanded state having a substantially spheroidal shape and an open structure;

(b) assembling the maintainer and the main inflatable chamber to form a maintainer and main inflatable chamber assembly having a substantially cylindrical shape;

(c) placing the maintainer and main inflatable chamber assembly in a collapsed condition adjacent the organ;

(d) inflating the main inflatable chamber to retract the organ into a retracted condition and to expand the maintainer to the expanded state; and (e) deflating the main inflatable chamber, the maintainer in the expanded state maintaining the organ in the retracted condition and providing access to the tissue.

6. The method of claim 5, additionally comprising a step of removing the main inflatable chamber from the body.

7. The method of claim 5, wherein, in the providing step:

the maintainer comprises plural strips of a malleable material arranged to form a curved surface of a cylinder, and in the assembling step, the main inflatable chamber is placed inside a space bounded by the curved surface of the maintainer.

8. The method of claim 5, wherein, in the providing step, the maintainer comprises:

a first hub and a second hub, each hub being cylindrical and having a curved outer surface; and plural strips of a malleable material, each strip having a first end and a second end, the first end being attached to the curved outer surface of the first hub, and the second end being attached to the curved outer surface of the second hub.

9. The method of claim 5, wherein, in the providing step, the maintainer comprises a hollow cylinder of a malleable material, the hollow cylinder having a curved sidewall, a first end, and a second end, the curved sidewall being pierced by plural longitudinal apertures each extending from a point adjacent to the first end to a point adjacent to the second end to form plural strips interconnecting the first end and the second end.

10. The method of claim 5, wherein:

in the providing step, a surgical instrument is additionally provided; and the method additionally comprises a step of treating the tissue using the surgical instrument passed through the open structure of the maintainer in the expanded state.

11. The method of claim 5, wherein: in the providing step:

the main inflatable chamber is bounded by an envelope releasably attached to a distal end of an elongate tube, and a surgical instrument is additionally provided; and the method additionally comprises steps of:

releasing the envelope from the elongate tube following the step of deflating the main inflatable chamber, and treating the tissue using the surgical instrument passed into the maintainer through the elongate tube and passed out of the maintainer through the open structure of the maintainer.

12. The method of claim 11, wherein:

in the placing step, a proximal end of the elongate tube is manipulated to place the maintainer and main inflatable chamber assembly adjacent to the organ;

in the inflating step, inflation fluid is passed into the main inflatable chamber through the elongate tube; and the method additionally comprises a step of withdrawing the envelope from the body following the releasing step.

* * * * *